US008987202B2

(12) United States Patent
Haaning et al.

(10) Patent No.: US 8,987,202 B2
(45) Date of Patent: *Mar. 24, 2015

(54) FACTOR VII OR FACTOR VIIA GLA DOMAIN VARIANTS

(75) Inventors: Jesper Mortensen Haaning, Birkeroed (DK); Kim Vilbour Andersen, Broenshoej (DK); Claus Bornaes, Hellerup (DK)

(73) Assignee: Bayer Healthcare LLC, Whippany, NJ (US)

( * ) Notice: Subject to any disclaimer, the term of this patent is extended or adjusted under 35 U.S.C. 154(b) by 717 days.

This patent is subject to a terminal disclaimer.

(21) Appl. No.: 11/424,035

(22) Filed: Jun. 14, 2006

(65) Prior Publication Data

US 2006/0241041 A1    Oct. 26, 2006

Related U.S. Application Data

(60) Division of application No. 11/021,239, filed on Dec. 22, 2004, which is a continuation-in-part of application No. PCT/DK2004/000428, filed on Jun. 18, 2004.

(60) Provisional application No. 60/479,780, filed on Jun. 19, 2003.

(30) Foreign Application Priority Data

Jun. 15, 2004 (DK) .................................. 2004 00930

(51) Int. Cl.
*A61K 38/00* (2006.01)
*C12N 9/64* (2006.01)
*A61K 38/48* (2006.01)

(52) U.S. Cl.
CPC .......... *C12N 9/6437* (2013.01); *A61K 38/4846* (2013.01); *C12N 9/647* (2013.01); *C12Y 304/21021* (2013.01)
USPC .................. 514/12; 514/2; 530/350; 530/300

(58) Field of Classification Search
None
See application file for complete search history.

(56) References Cited

U.S. PATENT DOCUMENTS

| | | |
|---|---|---|
| 4,784,950 A | 11/1988 | Hagen et al. |
| 4,904,584 A | 2/1990 | Shaw |
| 5,041,376 A | 8/1991 | Gething et al. |
| 5,093,317 A | 3/1992 | Lewis et al. |
| 5,180,583 A | 1/1993 | Hedner |
| 5,225,537 A | 7/1993 | Foster |
| 5,258,288 A | 11/1993 | Wydro et al. |
| 5,288,629 A | 2/1994 | Berkner |
| 5,460,950 A | 10/1995 | Barr et al. |
| 5,504,064 A | 4/1996 | Morrisey et al. |
| 5,516,640 A | 5/1996 | Watanabe et al. |
| 5,580,560 A | 12/1996 | Nicolaisen et al. |
| 5,648,254 A | 7/1997 | Mulvihill et al. |
| 5,788,965 A | 8/1998 | Berkner et al. |
| 5,817,788 A | 10/1998 | Berkner et al. |
| 5,824,634 A | 10/1998 | Merchant |
| 5,824,639 A | 10/1998 | Berkner |
| 5,833,982 A | 11/1998 | Berkner et al. |
| 5,837,843 A | 11/1998 | Smirnov et al. |
| 5,847,085 A | 12/1998 | Esmon et al. |
| 5,861,374 A | 1/1999 | Berkner et al. |
| 5,891,843 A | 4/1999 | Turecek et al. |
| 5,965,425 A | 10/1999 | Barr et al. |
| 5,986,079 A | 11/1999 | Barr et al. |
| 6,013,620 A | 1/2000 | Turecek et al. |
| 6,017,882 A | 1/2000 | Nelsestuen |
| 6,100,061 A | 8/2000 | Reiter et al. |
| 6,423,826 B1 | 7/2002 | Nelsestuen et al. |
| 6,475,725 B1 | 11/2002 | Reiter et al. |
| 6,693,075 B1 | 2/2004 | Nelsestuen |
| 6,747,003 B1 | 6/2004 | Nelsestuen |
| 6,762,286 B2 | 7/2004 | Nelsestuen |
| 6,806,063 B2 | 10/2004 | Pedersen et al. |
| 6,903,069 B2 | 6/2005 | Pingel et al. |
| 7,026,524 B2 | 4/2006 | Persson et al. |
| 7,220,837 B1 | 5/2007 | Nelsestuen |
| 2003/0100506 A1 | 5/2003 | Nelsestuen |
| 2003/0100740 A1 | 5/2003 | Persson et al. |
| 2003/0104978 A1 | 6/2003 | Persson et al. |
| 2003/0211094 A1 | 11/2003 | Nelsestuen |
| 2003/0211460 A1 | 11/2003 | Nelsestuen |
| 2005/0164932 A1 | 7/2005 | Haaning |
| 2006/0019336 A1 | 1/2006 | Pedersen |
| 2006/0111282 A1 | 5/2006 | Haaning |

(Continued)

FOREIGN PATENT DOCUMENTS

EP    0 296 413 A2    12/1988
EP    0 354 504 A2    2/1990

(Continued)

OTHER PUBLICATIONS

Guo et al. (PNAS, vol. 101, No. 25, pp. 9205-9210, 2004).*
Seffernick et al. (J. Bacteriology, vol. 183, pp. 2405-2410, 2001).*
Wells, (Biochemistry, vol. 29, pp. 8509-8517, 1990).*
J. Toomey et al., Localization of the Human Tissue Factor Recognition Determinant of Human Factor VIIa, *J. Biol. Chem.* 266(29):19198-19202 (1991).
Pending claims of U.S. Appl. No. 10/031,005, Nelsestuen, Parent application published as WO 00/66753, which is a national phase appn of WO 00/66753.

(Continued)

*Primary Examiner* — Hope Robinson

(57) ABSTRACT

Gla domain variants of human Factor VII or human Factor VIIa, comprising 1-15 amino acid modifications relative to the human Factor VII or human Factor VIIa sequence shown in SEQ ID NO:1, wherein a hydrophobic amino acid residue has been introduced by substitution in position 34; or having an amino acid substitution in position 36; and use of the variants for the treatment of intracerebral haemorrhage (ICH) or trauma.

31 Claims, 5 Drawing Sheets

(56) References Cited

U.S. PATENT DOCUMENTS

| | | | |
|---|---|---|---|
| 2006/0166874 A1 | 7/2006 | Haaning |
| 2006/0228782 A1 | 10/2006 | Pedersen |
| 2006/0240524 A1 | 10/2006 | Pedersen |
| 2006/0240525 A1 | 10/2006 | Pedersen |
| 2006/0240526 A1 | 10/2006 | Haaning |
| 2006/0241041 A1 | 10/2006 | Haaning |
| 2006/0252127 A1 | 11/2006 | Pedersen |
| 2006/0252128 A1 | 11/2006 | Haaning |
| 2006/0252689 A1 | 11/2006 | Pedersen |
| 2006/0252690 A1 | 11/2006 | Pedersen |
| 2006/0258585 A1 | 11/2006 | Pedersen |
| 2006/0270000 A1 | 11/2006 | Haaning |
| 2006/0270001 A1 | 11/2006 | Haaning |
| 2006/0270002 A1 | 11/2006 | Haaning |
| 2006/0276377 A1 | 12/2006 | Haaning |
| 2007/0054366 A1 | 3/2007 | Andersen |
| 2007/0117756 A1 | 5/2007 | Haaning |
| 2007/0142280 A1 | 6/2007 | Pedersen |

FOREIGN PATENT DOCUMENTS

| | | |
|---|---|---|
| EP | 0 370 205 A2 | 5/1990 |
| EP | 0 512 011 B1 | 11/1992 |
| WO | WO 88/10295 A1 | 12/1988 |
| WO | WO 91/11514 A1 | 8/1991 |
| WO | WO 92/15686 A1 | 9/1992 |
| WO | WO 94/27631 A1 | 12/1994 |
| WO | WO 96/00577 A1 | 1/1996 |
| WO | WO 98/32466 A1 | 7/1998 |
| WO | WO 98/35026 A1 | 8/1998 |
| WO | WO 99/03498 A1 | 1/1999 |
| WO | WO 99/03887 A1 | 1/1999 |
| WO | WO 99/20767 A1 | 4/1999 |
| WO | WO 99/66031 A2 | 12/1999 |
| WO | WO 00/26230 A1 | 5/2000 |
| WO | WO 00/26354 A1 | 5/2000 |
| WO | WO 00/28065 A1 | 5/2000 |
| WO | WO 00/54787 A1 | 9/2000 |
| WO | WO 00/66753 A2 | 11/2000 |
| WO | WO 01/58935 A2 | 8/2001 |
| WO | WO 01/83725 A1 | 11/2001 |
| WO | WO 02/02764 | 1/2002 |
| WO | WO 02/03075 | 1/2002 |
| WO | WO 02/22776 A2 | 3/2002 |
| WO | WO 02/29025 | 4/2002 |
| WO | WO 02/38162 A1 | 5/2002 |
| WO | WO 02/077218 A1 | 10/2002 |
| WO | WO 03/027147 A2 | 4/2003 |
| WO | WO 03/037932 A2 | 5/2003 |
| WO | WO 03/055512 A1 | 7/2003 |
| WO | WO 03/093465 A1 | 11/2003 |
| WO | WO 2004/029091 A2 | 4/2004 |
| WO | WO 2004/083361 A2 | 9/2004 |

OTHER PUBLICATIONS

Arnljots et al., "Prevention of experimental arterial thrombosis by topical administration of active site-inactivated factor VIIa," J. Vasc. Surg., 1997, 25(2):341-346.

Bauer, "Treatment of factor VII deficiency with recombinant factor VIIa," Haemostasis, 1996, 26 (Suppl. 1):155-158.

Broze et al., "Monoclonal anti-human factor VII antibodies. Detection in plasma of a second protein antigenically and genetically related to factor VII," J. Clin. Invest., 1985, 76:937-946.

Choudhri et al., "Targeted Inhibition of Intrinsic Coagulation Limits Cerebral Injury in Stroke without Increasing Intracerebral Hemorrhage," J. Exp. Med., 1999, 190:91-99.

Christiansen et al., "Hydrophobic Amino Acid Residues of Human Anticoagulation Protein C that Contribute to its Functional Binding to Phospholipid Vesicles," Biochemistry, 1995, 34:10376-10382.

Dackiw et al., "Prevention of endotoxin-induced mortality by antitissue factor immunization," Arch. Surg., 1996,131:1273-1278.

Dahlback, "Inherited Thrombophilia: Resistance to Activated Protein C as a Pathogenic Factor of Venous Thromboemolism," Blood, 1995, 85:607-614.

Database EMBL, "Coagulation factor VII (EC 3.4.21.21)(Serum prothrombin conversion accelerator)," "Bovine Factor VII. Its purification and complete amino acid sequence," ID FA7_BOVIN, Aug. 1, 1991 (3 pages).

"Docking of Tissue Factor and Factor VIIa Initiates Blood Coagulation," at http://www.sdsc.edu.IOTW/week46.96/ (1996).

Esmon et al., "Isolation of a membrane-bound cofactor for thrombin-catalyzed activation of protein C," J. Biol. Chem., 1982, 257:859-864.

Evans, Jr. and Nelsestuen, "Importance of cis-Proline 22 in the Membrane-Binding Conformation of Bovine Prothrombin," Biochemist, 1996, 35:8210-8215.

Evans and Nelsestuen, "Importance of Cis-Proline 22 and the Aromatic Stack (Residues 41-45) for Prothrombin-Membrane Binding," Protein Sci., 1996, 5(Suppl. 1):163, Abstract #606-S.

Felgner et al., "Lipofection: a highly efficient, lipid-mediated DNA-transfection procedure," Proc. Natl. Acad. Sci. USA, 1987, 84:7413-7417.

Fiore et al., "The biochemical basis for the apparent defect of soluble mutant tissue factor in enhancing the proteolytic activities of factor VIIa," J. Biol. Chem., 1994, 269:143-149.

Freedman et al., "Identification of the phospholipid binding site in the vitamin K-dependent blood coagulation protein factor IX," J. Biol. Chem., 1996, 271(27):16227-16236.

Furie and Furie, "The molecular basis of blood coagulation," Cell, 1988, 53:505-518.

Guo et al., "Protein Tolerance to random amino acid change," Proc. Natl. Acad. Sci. 101(25):9205-9210 (2004).

Han et al., "Isolation of a protein Z-dependent plasma protease inhibitor," Proc. Natl. Acad. Sci. USA, 1998, 95:9250-9255.

He et al., "Expression and functional characterization of chimeras between human and bovine vitamin-K-dependent protein-S-defining modules important for the species specificity of the activated protein C cofactor activity," Eur. J. Biochem., 1995, 227:433-440.

Hedner et al., "Recombinant Activated Factor VII in the Treatment of Bleeding Episodes in Patients with Inherited and Acquired Bleeding Disorders," Transfus. Med. Rev., 1993, 7:78-83.

Hope et al., "Production of Large Unilamellar Vesicles by a Rapid Extrusion Procedure. Characterization of Size Distribution, Trapped Volume and Ability to Maintain a Membrane Potential," Biochem. Biophys. Acta, 1985, 812:55-65.

Hoskins et al., "Cloning and characterization of human liver cDNA encoding a protein S precursor," Proc. Natl. Acad. Sci. USA, 1987,84:349-353.

Huang, ,"Studies on Phosphatidylcholine Vesicles. Formation and Physical Characteristics", Biochemistry, Biochemistry, 1969, 8:344-352.

Humphries et al., "Chemical methods of protein synthesis and modification," Curr. Opin. Biotechnol., 1991, 2(4):539-543.

Jurlander et al., "Recombinant Activated Factor VII (rFVIIa): Characterization, Manufacturing, and Clinical Development," Semin. Thromb. Hemos., 2001, 27(4):373-383.

Leff, "Genetically Stripped-Down Factor VIII Corrects Bleeding Disorder in Hemophiliac Mice," BioWorld Today, 1997, 8(209):1,6.

Lu and Nelsestuen, "Dynamic Features of Prothrombin Interaction with Phospholipid Vesicles of Different Size and Composition: Implications for Protein—Membrane Contact," Biochemistry, 1996, 35:8193-8200.

Lu and Nelsestuen, "The prothrombinase reaction: "mechanism switching" between Michaelis-Menten and non-Michaelis-Menten behaviors," Biochemistry, 1996, 35:8201-8209.

Martinez et al., "Underdecarboxylation of Vitamin K-Dependent Proteins: Occasionally Severe, Possibly Universal," Proceedings of the 49th ASMS Conference on Mass Spectrometry and Allied Topics, May 27-31, 2001, Chicago, Illinois, 2 pgs.

Matsubara et al., "A receptor tyrosine kinase, Sky, and its ligand Gas 6 are expressed in gonads and support primordial germ cell growth or survival in culture," Dev. Biol., 1996, 180:499-510.

Mayer et al., "Prothrombin Association with Phospholipid Monolayers," Biochemistry, 1983, 22(2):316-321.

Mayer, "Ultra-early hemostatic therapy for intracerebral hemorrhage," Stroke 2003, 34:224-229.

(56) References Cited

OTHER PUBLICATIONS

McDonald et al., "Comparison of Naturally Occurring Vitamin K-dependent Proteins: Correlation of Amino Acid Sequences and Membrane Binding Properties Suggests a Membrane Contact Site," Biochemistry, 1997, 36:5120-5127.

McDonald et al., "Ionic Properties of Membrane Association by Vitamin K-Dependent Proteins: The Case for Univalency," Biochemistry, 1997, 36(50):15589-15598.

Morrissey et al., "Quantitation of Activated Factor VII Levels in Plasma Using a Tissue Factor Mutant Selectively Deficient in Promoting Factor VII Activation," Blood, 1993, 81(3):734-744.

Muir et al., "The chemical synthesis of proteins," Curr. Opin. Biotechnol., 1993, 4(4):420-427.

Nakagaki et al., "Initiation of the Extrinsic Pathway of Blood Coagulation: Evidence for the Tissue Factor Dependent Autoactivation of Human Coagulation Factor VII," Biochemistry, 1991, 30:10819-10824.

Nelsestuen et al., "Membrane association with multiple calcium ions: vitamin-K-dependent proteins, annexins and pentraxins," Current Opinion in Structural Biology 9:433-437 (1999).

Nelsestuen, "Enhancement of Vitamin-K-Dependent Protein Function by Modification of the gamma-Carboxyglutamic Acid Domain: Studies of Protein C and Factor VII," Trends Cardiovasc. Med. 9(6):162-167 (1999).

Nelsestuen et al., "Vitamin K-Dependent Proteins," in 58 Vitamins and Hormones: Advances in Research and Applications (Gerald Litwack ed., Academic Press, 2000) pp. 355-389.

Nelsestuen et al., "Equilibria Involved in Prothrombin- and Blood Clotting Factor X-Membrane Binding," Biochemistry, 1977, 16(19):4164-4171.

Nelsestuen and Suttie, "Properties of Asialo and Aglycoprothrombin," Biochem. Biophys. Res. Commun., 1971, 45:198-203.

Nicolaes et al., "A prothrombinase-based assay for detection of resistance to activated protein C," Thromb. Haemost., 1996, 76:404-410.

Nicolaisen et al., "Immunological aspects of recombinant factor VIIa (rFVIIa) in clinical use," Thromb. Haemost., 1996, 76:200-204.

Okafuji et al., EMBL Data Library, Accession No. S18994, Sep. 10, 1999 (protein C activated precursor, sequence) (Score Search).

Perera et al., "Trans-cis Isomerization of Proline 22 in Bovine Prothrombin Fragment 1: A Surprising Result of Structural Characterization," Biochemistry, 1998, 37:10920-10927.

Petersen et al., "Quenching of the amidolytic activity of one-chain tissue-type plasminogen activator by mutation of lysine-416," Biochemistry, 1990, 29:3451-3457.

Petrovan et al., "Residue Met$^{158}$ contributes to the labile enzyme conformation of coagulation factor VIIa," J. Biol. Chem. 2001, 276(9):6616-6620.

Ratcliffe et al., "The Importance of Specific γ-Carboxyglutamic Acid Residues in Prothrombin," J. Biol. Chem., 1993, 268(32):24339-24345.

Resnick and Nelsestuen, "Prothrombin-Membrane Interaction. Effects of Ionic Strength, pH, and Temperature," Biochemistry, 1980, 19(13):3028-3033.

Rezaie and Esmon, "The function of calcium in protein C activation by thrombin and the thrombin-thrombomodulin complex can be distinguished by mutational analysis of protein C derivatives," J. Biol. Chem., 1992, 267:26104-26109.

Sakai et al., "The γ-Carboxyglutamic Acid Domain of Human Factor VIIa is Essential for Its Interaction with Cell Surface Tissue Factor," J. Biol. Chem., 1990, 265(4):1890-1894.

Schmidel et al., "Organization of the Human Protein S Genes," J. Biol. Chem., 1990, 29(34):7845-7852.

Schulman et al., "Feasibility of using recombinant factor VIIa in continuous infusion," Thromb. Haemost., 1996, 75(3):432-436.

Schwalbe et al., "Protein Structural Requirements and Properties of Membrane Binding by γ-Carboxyglutamic Acid-containing Plasma Proteins and Peptides," J. Biol. Chem., 1989, 264:20288-20296.

Seffernick et al., "Melamine Deaminase and Atrazine Chlorohydrolase: 98 Percent Identical but Functionally Different," J. Bacteriol. 183(8):2405-2410 (2001).

Seshadri et al., "Differences in the Metal Ion Structure between Sr- and Ca-Prothrombin Fragment 1," Biochemistry, 1994, 33:1087-1092.

Shen et al., "Enhancing the Activity of Protein C by Mutagenesis to Improve the Membrane-Binding Site: Studies Related to Proline 10," Biochemistry, 1997, 36(51):16025-16031.

Shen et al., "Enhancement of Human Protein C Function by Site-directed Mutagenesis of the γ-Carboxyglutamic Acid Domain," J. Biol. Chem., 1998, 273(47):31086-31091.

Smirnov et al., "A Chimeric Protein C Containing the Prothrombin Gla Domain Exhibits Increased Anticoagulant Activity and Altered Phospholipid Specificity," J. Biol. Chem., 1998, 273(15):9031-9040.

Thariath et al., "Highly conserved residue arginine-15 is required for the $Ca^{2+}$-dependent properties of the γ-carboxyglutamic acid domain of human anticoagulation Protein C and activated Protein C," Biochem. J., 1997, 322:309-315.

Thim et al., "Amino Acid Sequence and Posttranslational Modification of Human Factor VIIa from Plasma and Transfected Baby Hamster Kidney Cells," Biochemistry, 1988, 27:7785-7793.

Thomsen et al., "Pharmacokinetics of recombinant factor VIIa in the rat—a comparison of bio-, immuno- and isotope assays," Thromb. Haemost., 1993, 70(3):458-464.

Vallette et al., "Construction of mutant and chimeric genes using the polymerase chain reaction," Nucleic Acids Res., 1989, 17(2):723-733.

Vrana et al., "Expression of tissue factor in tumor stroma correlates with progression to invasive human breast cancer: paracrine regulation by carcinoma cell-derived members of the transforming growth factor beta family," Cancer Res., 56:5063-5070 (1996).

Weber et al., "Modifications of Bovine Prothrombin Fragment 1 in the Presence and Absence of Ca(II) Ions," J. Biol. Chem., 1992, 267(7):4564-4569.

Wei et al., "Kinetic and Mechanistic Analysis of Prothrombin-Membrane Binding by Stopped-Flow Light Scattering," Biochemistry, 1982, 21:1949-1959.

Wells, "Additivity of Mutational Effects in Proteins," Biochem. 29(17):8509-8517 (1990).

Welsch et al., "Chemical Modification of Prothrombin Fragment 1: Documentation of Sequential, Two-Stage Loss of Protein Function," Biochemistry, 1988, 27:4933-4938.

Welsch and Nelsestuen, "Amino-terminal alanine functions in a calcium-specific process essential for membrane binding by prothrombin fragment 1," Biochemistry, 1988, 27:4939-4945.

Yan et al., "Characterization and Novel Purification of Recombinant Human Protein C from Three Mammalian Cell Lines," Bio/Technology, 1990, 8:655-661.

Zhang et al., "Role of Individual γ-Caboxyglutamic Acid Residues of Activated Human Protein C in Defining its In Vitro Anticoagulant Activity," Blood, 1992, 80(4):942-952.

Zwaal et al., "Lipid-protein interactions in blood coagulation," Biochimica et Biophysica Acta, 1998, 1376:433-453.

Bharadwaj, D., et al., "Factor VII Central—A Novel Mutation in the Catalytic Domain that Reduces Tissue Factor Binding, Impairs Activation by Factor XA, and Abolishes Amidolytic and Coagulant Activity," J. Biological Chemistry 271(48):30685-30691 (1996).

Bjoern, S., et al., "Human Plasma and Recombinant Factor VII—Characterization of O-Glycosylations at Serine Residues 52 and 60 and Effects of Site-Directed Mutagenesis of Serine 52 to Alanine," J. Biological Chemistry 266(17):11051-11057 (1991).

Chang, J-Y., et al., "Replacing the First Epidermal Growth Factor-like Domain of Factor IX with That of Factor VII Enhances Activity In Vitro and in Canine Hemophilia B," J. Clin. Invest. 100(4):886-892 (1997).

Chang, Y-J., et al., "Engineered Recombinant Factor VII $Q^{217}$ Variants with Altered Inhibitor Specificities," Biochemistry 38:10940-10948 (1999).

Cheung, W.F. et al., "Localization of an Epitope of Calcium-Dependent Monoclonal Antibody to the N-Terminal Region of the Gla Domain of Human Factor VII", Thrombosis Research, 79(2):199-206 (1995).

(56) References Cited

OTHER PUBLICATIONS

Cheung, W.F. et al., "Localization of a metal-dependent epitope to the amino terminal residues 33-40 of human factor IX", *Thrombosis Research*, 80(5):419-427 (1995).
Database EMBL, "*Gallus gallus* anticoagulant protein C precursor (PROC) mRNA, complete cds", Database Accession No. AF465270, Feb. 2, 2003.
Database UNIPROT, "Coagulation factor VII (EC 3.4.21.21) (Serum prothrombin conversion accelerator)", Database Accession No. P22457, Aug. 1, 1991.
Dickinson, C.D., et al., "Identification of surface residues mediating tissue factor binding and catalytic function of the serine protease factor VIIa," *Proc. Natl. Acad. Sci. USA* 93:14379-14384 (1996).
Dickinson, C.D., et al., "Active Site Modification of Factor VIIa Affects Interactions of the Protease Domain with Tissue Factor," *J. Biological Chemistry* 272(32):19875-19879 (1997).
Dickinson, C. D. et al., "Influence of Cofactor Binding and Active Site Occupancy on the Conformation of the Macromolecular Substrate Exosite of Factor VIIa", *J. Mol. Biol.* 277:959-971 (1998).
Dutton R.P. et al., "Factor VIIa for correction of traumatic coagulopathy", *J. Trauma* 57(4):709-719 (2004).
Hedner, U. "NovoSeven as a universal haemostatic agent." *Blood Coagul. Fibrinolysis* 11 Suppl 1:S107-S111 (2000).
Higashi, S. et al. "Molecular mechanism of tissue factor-mediated acceleration of factor VIIa activity," *J. Biol. Chem.* 271(43):26569-74 (1996).
Huang, Q., et al., "Substrate Recognition by Tissue Factor-Factor VIIa—Evidence for Interaction of Residues Lys [165] and Lys [166] of Tissue Factor with the 4-Carboxyglutamate-Rich Domain of Factor X," *J. Biological Chemistry* 271(36):21752-21757 (1996).
Iino, M., et al., "Functional Consequences of Mutations in Ser-52 and Ser-60 in Human Blood Coagulation Factor VII," *Archives Biochem. Biophys.* 352(2):182-192 (1998).
Iakhiaev, A. et al. "The role of catalytic cleft and exosite residues of factor VIIa for complex formation with tissue factor pathway inhibitor", *Thromb. Haemost.* 85(3):458-463 (2001).
Jin, J., et al., "Factor VIIa's First Epidermal Growth Factor-like Domain's Role in Catalytic Activity," *Biochemistry* 38:1185-1192 (1999).
Jin, J. et al., "Four Loops of the Catalytic Domain of Factor VIIa Mediate the Effect of the First EGF-like Domain Substitution on Factor VIIa Catalytic Activity", *J. Mol. Biol.* 307:1503-1517 (2001).
Kelly, C.R., et al., "$Ca^{2+}$ Binding to the First Epidermal Growth Factor Module of Coagulation Factor VIIa Is Important for Cofactor Interaction and Proteolytic Function," *J. Biological Chemistry* 272(28):17467-17472 (1997).
Kemball-Cook, G., et al., "Coagulation Factor VII $Gln^{100}Arg$—Amino Acid Substitution at the Epidermal Growth Factor 2-Protease Domain Interface Results in Severely Reduced Tissue Factor Binding and Procoagulant Function," *J. Biological Chemistry* 273(14):8516-8521 (1998).
Leonard, B.J.N., et al., "Activation and Active Site Occupation Alter Conformation in the Region of the First Epidermal Growth Factor-like Domain of Human Factor VII," *J. Biological Chemistry* 275(45):34894-34900 (2000).
Mayer, S.A. "Ultra-early hemostatic therapy for intracerebral hemorrhage," *Stroke* 34(1):224-229 (2003).
Nelsestuen, G.L. et al. "Elevated function of blood clotting factor VIIa mutants that have enhanced affinity for membranes. Behavior in a diffusion-limited reaction," *J. Biol. Chem.* 276(43):39825-39831 (2001).
Neuenschwander, P.F. et al., "Alteration of the Substrate and Inhibitor Specificities of Blood Coagulation Factor VIIa: Importance of Amino Acid Residue K192", *Biochemistry* 34:8701-8707 (1995).
Novo Nordisk Stock Exchange Announcement, Jun. 22, 2004.
Persson, E., et al., "Site-directed mutagenesis but not γ-carboxylation of Glu-35 in factor VIIa affects the association with tissue factor," *FEBS Letters* 385:241-243 (1996).
Persson, E., "Characterization of the interaction between the light chain of factor VIIa and tissue factor," *FEBS Letters* 413:359-363 (1997).
Persson, E., et al., "$Ca^{2+}$ Binding to the First Epidermal Growth Factor-like Domain of Factor VIIa Increases Amidolytic Activity and Tissue Factor Affinity," *J. Biological Chemistry* 272(32):19919-19924 (1997).
Petersen, L.C., et al., "Binding of $Zn^{2+}$ to a $Ca^{2+}$ loop allosterically attenuates the activity of factor VIIa and reduces its affinity for tissue factor," *Protein Science* 9:859-866 (2000).
Petrovan, R.J., et al., "Role of Residue $Phe^{225}$ in the Cofactor-Mediated, Allosteric Regulation of the Serine Protease Coagulation Factor VIIa," *Biochemistry* 39:14457-14463 (2000).
Petrovan, R.J., et al., "Residue Met(156) contributes to the labile enzyme conformation of coagulation factor VIIa" *J. Biol. Chem.* 276(9):6616-6620 (2001).
Ruf, W., et al., "Importance of Factor VIIa Gla-Domain Residue Arg-36 for Recognition of the Macromolecular Substrate Factor X Gla-Domain," *Biochemistry* 38:1957-1966 (1999).
Shah, A.M., et al., "Manipulation of the membrane binding site of vitamin K-dependent proteins: Enhanced biological function of human factor VII," *Proc. Natl. Acad. Sci. USA* 95:4229-4234 (1998).
Shobe, J., et al., "Macromolecular Substrate Affinity for the Tissue Factor—Factor VIIa Complex is Independent of Scissile Bond Docking," *J. Biological Chemistry* 274(34):24171-24175 (1999).
Shobe, J., et al., "Regulation of the Catalytic Function of Coagulation Factor VIIa by a Conformational Linkage of Surface Residue Glu 154 to the Active Site," *Biochemistry* 38:2745-2751 (1999).
Sorensen, B.B. et al. "Incorporation of an active site inhibitor in factor VIIa alters the affinity for tissue factor," *J. Biol. Chem.* 272(18):11863-11868 (1997).
Sridhara S. et al. "Activation of a recombinant human factor VII structural analogue alters its affinity of binding to tissue factor," *Am. J. Hematol.* 53(2):66-71 (1996).
Zhang, E. et al., "Structure of Extracellular Tissue Factor Complexed with Factor VIIa Inhibited with a BPTI Mutant," *J. Mol. Biol.* 285(5):2089-2104 (1999).
Harvey, Stephen B., et al., "Mutagenesis of the γ-carboxyglutamic acid domain of human factor VII to generate maximum enhancement of the membrane contact site," The Journal of Biological Chemistry 278(10):8363-8369 (Mar. 2003).
Henderson, Nicole et al., "Response of factor VII and IX-deficient blood to wild type and high membrane affinity mutant factor VIIa in an in vitro whole blood clotting assay: possible correlation to clinical outcome," Thromb Haemost 88:98-103 (2002).
Stone, Matthew et al., "Unusual benefits of macromolecular shielding by polyethylene glycol for reactions at the diffusional limit: the case of factor VIIai and tissue factor," Biochemistry 41:15820-15825 (2002).
Zhang, Li et al., "The contributions of individual γ-carboxyglutamic acid residues in the calcium-dependent binding of recombinant human protein c to acidic phospholipid vesicles," The Journal of Biological Chemistry 268 (16):12040-12045 (Jun. 1993).
U.S. Appl. No. 11/279,541, Pedersen et al., Unpublished.

\* cited by examiner

FACTOR VII OR FACTOR VIIA GLA DOMAIN VARIANTS

CROSS-REFERENCE TO RELATED APPLICATIONS

This application is a divisional application of U.S. patent application Ser. No. 11/021,239 filed on Dec. 22, 2004, which is a continuation-in-part application of International Patent Application No. PCT/DK2004/000428 filed on Jun. 18, 2004, which claims the benefit of U.S. Provisional Patent Application Ser. No. 60/479,780 filed on Jun. 19, 2003 and of Denmark Patent Application No. PA 2004 00930 filed on Jun. 15, 2004, the disclosures of each of which are incorporated by reference herein in their entirety for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to novel Gla domain variants of Factor FVII (FVII) or Factor VIIa (FVIIa) polypeptides, as well as the use of such polypeptide variants in therapy, in particular for the treatment of a variety of coagulation-related disorders.

BACKGROUND OF THE INVENTION

Blood coagulation is a process consisting of a complex interaction of various blood components (or factors) that eventually results in a fibrin clot. Generally, the blood components participating in what has been referred to as the "coagulation cascade" are proenzymes or zymogens, i.e. enzymatically inactive proteins that are converted into an active form by the action of an activator. One of these coagulation factors is FVII.

FVII is a vitamin K-dependent plasma protein synthesized in the liver and secreted into the blood as a single-chain glycoprotein with a molecular weight of 53 kDa (Broze & Majerus, *J. Biol. Chem.* 1980; 255:1242-1247). The FVII zymogen is converted into an activated form (FVIIa) by proteolytic cleavage at a single site, R152-I153, resulting in two chains linked by a single disulfide bridge. FVIIa in complex with tissue factor (FVIIa complex) is able to convert both factor IX (FIX) and factor X (FX) into their activated forms, followed by reactions leading to rapid thrombin production and fibrin formation (Østerud & Rapaport, *Proc Natl Acad Sci USA* 1977; 74:5260-5264).

FVII undergoes post-translational modifications, including vitamin K-dependent carboxylation resulting in ten γ-carboxyglutamic acid residues in the N-terminal region of the molecule. Thus, residues number 6, 7, 14, 16, 19, 20, 25, 26, 29 and 35 shown in SEQ ID NO:1 are γ-carboxyglutamic acid residues in the Gla domain important for FVII activity. Other post-translational modifications include sugar moiety attachment at two naturally occurring N-glycosylation sites at position 145 and 322, respectively, and at two naturally occurring O-glycosylation sites at position 52 and 60, respectively.

The gene coding for human FVII (hFVII) has been mapped to chromosome 13 at q34-qter 9 (de Grouchy et al., *Hum Genet* 1984; 66:230-233). It contains nine exons and spans 12.8 Kb (O'Hara et al., *Proc Natl Acad Sci USA* 1987; 84:5158-5162). The gene organisation and protein structure of FVII are similar to those of other vitamin K-dependent procoagulant proteins, with exons 1a and 1b encoding for signal sequence; exon 2 the propeptide and Gla domain; exon 3 a short hydrophobic region; exons 4 and 5 the epidermal growth factor-like domains; and exon 6 through 8 the serine protease catalytic domain (Yoshitake et al., *Biochemistry* 1985; 24: 3736-3750).

Reports exist on experimental three-dimensional structures of hFVIIa (Pike et al., *Proc Natl Acad Sci USA*, 1999; 96:8925-30 and Kemball-Cook et al., *J. Struct. Biol.*, 1999; 127:213-223); of hFVIIa in complex with soluble tissue factor using X-ray crystallographic methods (Banner et al., *Nature*, 1996; 380:41 and Zhang et al., *J. Mol. Biol.*, 1999; 285: 2089); and of smaller fragments of hFVII (Muranyi et al., *Biochemistry*, 1998; 37:10605 and Kao et al., *Biochemistry*, 1999; 38:7097).

Relatively few protein-engineered variants of FVII have been reported (Dickinson & Ruf, *J Biol Chem*, 1997; 272: 19875-19879; Kemball-Cook et al., *J Biol Chem*, 1998; 273: 8516-8521; Bharadwaj et al., *J Biol Chem*, 1996; 271:30685-30691; Ruf et al., *Biochemistry*, 1999; 38:1957-1966).

Reports exist on expression of FVII in BHK or other mammalian cells (WO 92/15686, WO 91/11514 and WO 88/10295) and co-expression of FVII and kex2 endoprotease in eukaryotic cells (WO 00/28065).

Commercial preparations of recombinant human FVIIa (rhFVIIa) are sold under the trademark NovoSeven®. NovoSeven® is indicated for the treatment of bleeding episodes in hemophilia A or B patients. NovoSeven® is the only rhFVIIa for effective and reliable treatment of bleeding episodes currently available on the market.

Mayer (*Stroke*, 2003, 34:224-229) speculated that ultra-early hemostatic treatment of intracerebral haemorrhage (ICH), given within 3-4 hours of onset, may arrest bleeding and minimize hematoma growth after ICH. On Jun. 22, 2004, it was reported in a stock exchange announcement by Novo Nordisk (Denmark) that NovoSeven® was found to provide a significantly improved neurological and functional outcome in the treatment of ICH. However, it was also reported that the treatment was associated with a non-significant increase in thromboembolic events.

An inactive form of FVII in which arginine 152 and/or isoleucine 153 are modified has been reported in WO 91/11514. These amino acids are located at the activation site. WO 96/12800 describes inactivation of FVIIa by a serine proteinase inhibitor. Inactivation by carbamylation of FVIIa at the α-amino acid group I153 has been described by Petersen et al., *Eur J Biochem*, 1999; 261:124-129. The inactivated form is capable of competing with wild-type FVII or FVIIa for binding to tissue factor and inhibiting clotting activity. The inactivated form of FVIIa is suggested to be used for treatment of patients suffering from hypercoagulable states, such as patients with sepsis or at risk of myocardial infarction or thrombotic stroke.

In connection with treatment of uncontrolled bleedings such as trauma it is believed that FVIIa is capable of activating FX to FXa without binding to tissue factor, and this activation reaction is believed to occur primarily on activated blood platelets (Hedner et al. *Blood Coagulation & Fibrinolysis*, 2000; 11; 107-111). However, hFVIIa or rhFVIIa has a low activity towards FX in the absence of tissue factor and, consequently, treatment of uncontrolled bleeding, for example in trauma patients, requires relatively high and multiple doses of hFVIIa or rhFVIIa. Therefore, in order to treat uncontrolled bleedings more efficiently (to minimize blood loss) there is need for improved FVIIa molecules which possess a high activity toward FX in the absence of tissue factor. Such improved FVIIa molecules should exhibit a lowered clotting time (faster action/increased clotting activity) as compared to rhFVIIa when administered in connection with uncontrolled bleedings.

Gla domain variants of FVII/FVIIa have been disclosed in WO 99/20767, U.S. Pat. No. 6,017,882 and WO 00/66753, where some residues located in the Gla domain were identified as being important for phospholipid membrane binding and hence FX activation. In particular, it was found that the residues 10 and 32 were critical and that increased phospholipid membrane binding affinity, and hence increased FX activation, could be achieved by performing the mutations P10Q and K32E. In particular, it was found that FX activation was enhanced as compared to rhFVIIa at marginal coagulation conditions, such as under conditions where a low level of tissue factor is present.

WO 01/58935 discloses a new strategy for developing FVII or FVIIa molecules having inter alia an increased half-life by means of directed glycosylation or PEGylation.

WO 03/093465 discloses FVII or FVIIa variants having certain modifications in the Gla domain and having one or more N-glycosylation sites introduced outside the Gla domain.

WO 2004/029091 discloses FVII or FVIIa variants having certain modifications in the tissue factor binding site.

The present inventors have now identified further residues in the Gla domain which further increase the phospholipid membrane binding affinity and hence further increase FX activation. The FVII or FVIIa variants of the invention may also exhibit reduced tissue factor binding affinity.

The object of the present invention is to provide improved FVII or FVIIa molecules (FVII or FVIIa variants) which are capable of activating FX to FXa more efficiently than hFVIIa, rhFVIIa or [P10Q+K32E]rhFVIIa. In particular, it is an object of the present invention to provide improved FVII or FVIIa molecules (FVII or FVIIa variants) which are capable of activating FX to FXa more efficiently than hFVIIa, rhFVIIa or [P10Q+K32E]rhFVIIa in the absence of tissue factor. These objects are addressed by the FVII or FVIIa variants provided herein.

BRIEF DISCLOSURE OF THE INVENTION

In a first aspect the present invention relates to a Factor VII (FVII) or Factor VIIa (FVIIa) polypeptide variant having an amino acid sequence comprising 1-15 amino acid modifications relative to human Factor VII (hFVII) or human Factor VIIa (hFVIIa) with the amino acid sequence shown in SEQ ID NO:1, wherein a hydrophobic amino acid residue has been introduced by substitution in position 34.

In a second aspect the invention relates to a Factor VII (FVII) or Factor VIIa (FVIIa) polypeptide variant having an amino acid sequence comprising 1-15 amino acid modifications relative to human Factor VII (hFVII) or human Factor VIIa (hFVIIa) with the amino acid sequence shown in SEQ ID NO:1, wherein the amino acid sequence comprises an amino acid substitution in position 36.

In a third aspect the invention relates to a Factor VII (FVII) or Factor VIIa (FVIIa) polypeptide variant having an amino acid sequence comprising 3-15 amino acid modifications relative to human Factor VII (hFVII) or human Factor VIIa (hFVIIa) having the amino acid sequence shown in SEQ ID NO:1, wherein amino acid sequence comprises an amino acid substitution in positions 10 and 32 and at least one further amino acid substitution in a position selected from the group consisting of positions 74, 77 and 116.

Further aspects of the invention relate to a nucleotide sequence encoding the polypeptide variants of the invention, an expression vector comprising the nucleotide sequence, and a host cell comprising the nucleotide sequence or expression vector.

Still further aspects of the invention relate to a pharmaceutical composition comprising the polypeptide variants of the invention, use of the polypeptide variants of the invention or the pharmaceutical composition of the invention as a medicament, as well as methods of treatment using the polypeptide variants or pharmaceutical compositions of the invention. In a particular aspect, the polypeptide variants of the invention are used for the treatment of intracerebral haemorrhage or traumatic brain injury.

Further aspects of the present invention will be apparent from the description below as well as from the appended claims.

DETAILED DISCLOSURE OF THE INVENTION

Definitions

Figure 1:
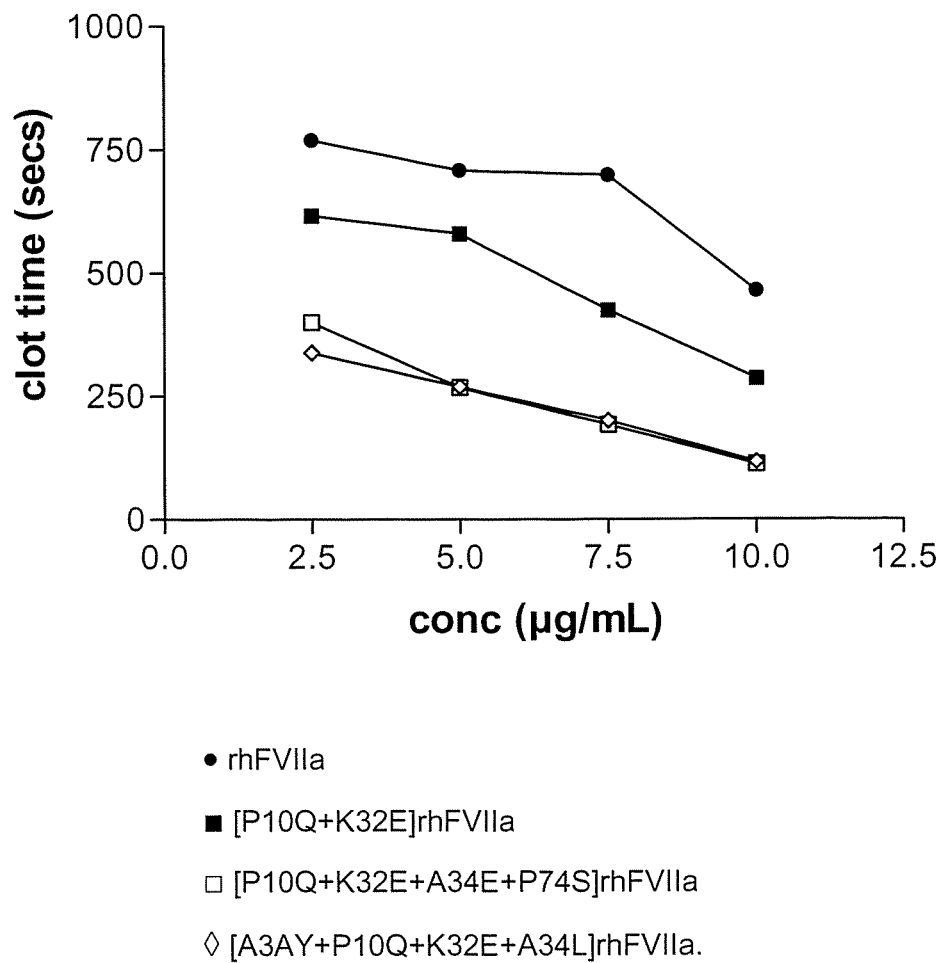
FIG. 1 shows the clotting time vs. concentration for variants of the invention when assayed in the "Whole Blood Assay".

In the context of the present description and claims the following definitions apply:

The term "FVII" or "FVII polypeptide" refers to a FVII molecule provided in single chain form. One example of a FVII polypeptide is the wild-type human FVII (hFVII) having the amino acid sequence shown in SEQ ID NO:1. It should be understood, however, that the term "FVII polypeptide" also covers hFVII-like molecules, such as fragments or variants of SEQ ID NO:1, in particular variants where the sequence comprises at least one, such as up to 15, preferably up to 10, amino acid modifications as compared to SEQ ID NO:1.

The term "FVIIa" or "FVIIa polypeptide" refers to a FVIIa molecule provided in its activated two-chain form. When the amino acid sequence of SEQ ID NO:1 is used to describe the amino acid sequence of FVIIa it will be understood that the peptide bond between R152 and I153 of the single-chain form has been cleaved, and that one of the chains comprises amino acid residues 1-152, the other chain comprises amino acid residues 153-406.

The terms "rFVII" and "rFVIIa" refer to FVII and FVIIa polypeptides produced by recombinant techniques.

The terms "hFVII" and "hFVIIa" refer to human wild-type FVII and FVIIa, respectively, having the amino acid sequence shown in SEQ ID NO:1

The terms "rhFVII" and "rhFVIIa" refer to human wild-type FVII and FVIIa, having the amino acid sequence shown in SEQ ID NO:1, produced by recombinant means. An example of rhFVIIa is NovoSeven®.

When used herein, the term "Gla domain" is intended to cover amino acid residues 1 to 45 of SEQ ID NO:1.

Accordingly, the term "position located outside the Gla domain" covers amino acid residues 46-406 of SEQ ID NO:1.

The abbreviations "FX", "TF" and "TFPI" mean Factor X, Tissue Factor and Tissue Factor Pathway Inhibitor, respectively.

The term "protease domain" is used about residues 153-406 counted from the N-terminus.

The term "catalytic site" is used to mean the catalytic triad consisting of S344, D242 and H193 of the polypeptide variant.

The term "parent" is intended to indicate the molecule to be modified/improved in accordance with the present invention. Although the parent polypeptide to be modified by the present invention may be any FVII or FVIIa polypeptide, and thus be derived from any origin, e.g. a non-human mammalian origin, it is preferred that the parent polypeptide is hFVII or hFVIIa.

A "variant" is a polypeptide which differs in one or more amino acid residues from its parent polypeptide, normally in 1-15 amino acid residues (e.g. in 1, 2, 3, 4, 5, 6, 7, 8, 9, 10, 11, 12, 13, 14 or 15 amino acid residues), such as in 1-10 amino acid residues, e.g. in 1-8, 1-6, 1-5 or 1-3 amino acid residues. Normally, the parent polypeptide is hFVII or hFVIIa.

The term "conjugate" (or interchangeably "conjugated polypeptide") is intended to indicate a heterogeneous (in the sense of composite or chimeric) molecule formed by the covalent attachment of one or more polypeptides to one or more non-polypeptide moieties such as polymer molecules, lipophilic compounds, sugar moieties or organic derivatizing agents. Preferably, the conjugate is soluble at relevant concentrations and conditions, i.e. soluble in physiological fluids such as blood. Examples of conjugated polypeptides of the invention include glycosylated and/or PEGylated polypeptides.

The term "covalent attachment" or "covalently attached" means that the polypeptide variant and the non-polypeptide moiety are either directly covalently joined to one another, or else are indirectly covalently joined to one another through at least one intervening moiety such as a bridge, spacer, or linkage moiety.

The term "non-polypeptide moiety" is intended to mean a molecule, different from a peptide polymer composed of amino acid monomers and linked together by peptide bonds, which molecule is capable of conjugating to an attachment group of the polypeptide variant of the invention. Preferred examples of such molecules include polymer molecules, sugar moieties, lipophilic compounds or organic derivatizing agents. When used in the context of a conjugated variant of the invention it will be understood that the non-polypeptide moiety is linked to the polypeptide part of the conjugated variant through an attachment group of the polypeptide. As explained above, the non-polypeptide moiety can be directly or indirectly covalently joined to the attachment group.

A "polymer molecule" is a molecule formed by covalent linkage of two or more monomers, wherein none of the monomers is an amino acid residue, except where the polymer is human albumin or another abundant plasma protein. The term "polymer" may be used interchangeably with the term "polymer molecule". The term is also intended to cover carbohydrate molecules attached by in vitro glycosylation, i.e. a synthetic glycosylation performed in vitro normally involving covalently linking a carbohydrate molecule to an attachment group of the polypeptide variant, optionally using a cross-linking agent.

The term "sugar moiety" is intended to indicate a carbohydrate-containing molecule comprising one or more monosaccharide residues, capable of being attached to the polypeptide variant (to produce a polypeptide variant conjugate in the form of a glycosylated polypeptide variant) by way of in vivo glycosylation. The term "in vivo glycosylation" is intended to mean any attachment of a sugar moiety occurring in vivo, i.e. during posttranslational processing in a glycosylating cell used for expression of the polypeptide variant, e.g. by way of N-linked and O-linked glycosylation. The exact oligosaccharide structure depends, to a large extent, on the glycosylating organism in question.

An "N-glycosylation site" has the sequence N—X—S/T/C, wherein X is any amino acid residue except proline, N is asparagine and S/T/C is either serine, threonine or cysteine, preferably serine or threonine, and most preferably threonine. Preferably, the amino acid residue in position +3 relative to the asparagine residue is not a proline residue.

An "O-glycosylation site" is the OH-group of a serine or threonine residue.

The term "attachment group" is intended to indicate a functional group of the polypeptide variant, in particular of an amino acid residue thereof or a carbohydrate moiety, capable of attaching a non-polypeptide moiety such as a polymer molecule, a lipophilic molecule, a sugar moiety or an organic derivatizing agent. Useful attachment groups and their matching non-polypeptide moieties are apparent from the table below.

| Attachment group | Amino acid | Examples of non-polypeptide moiety | Conjugation method/-Activated PEG | Reference |
|---|---|---|---|---|
| —NH$_2$ | N-terminal, Lys | Polymer, e.g. PEG, with amide or imine group | mPEG-SPA Tresylated mPEG | Nektar Therapeutics Delgado et al, Critical reviews in Therapeutic Drug Carrier Systems 9(3,4): 249–304 (1992) |
| —COOH | C-terminal, Asp, Glu | Polymer, e.g. PEG, with ester or amide group | mPEG-Hz | Nektar Therapeutics |
| | | Carbohydrate moiety | In vitro coupling | |

| Attachment group | Amino acid | Examples of non-polypeptide moiety | Conjugation method/-Activated PEG | Reference |
|---|---|---|---|---|
| —SH | Cys | Polymer, e.g. PEG, with disulfide, maleimide or vinyl sulfone group | PEG-vinylsulphone PEG-maleimide | Nektar Therapeutics Delgado et al, Critical reviews in Therapeutic Drug Carrier Systems 9(3,4): 249–304 (1992) |
| | | Carbohydrate moiety | In vitro coupling | |
| —OH | Ser, Thr, Lys, OH— | Sugar moiety | In vivo O-linked glycosylation | |
| | | PEG with ester, ether, carbamate, carbonate | | |
| —CONH$_2$ | Asn as part of an N-glycosylation site | Sugar moiety | In vivo N-glycosylation | |
| | | Polymer, e.g. PEG | | |
| Aromatic residue | Phe, Tyr, Trp | Carbohydrate moiety | In vitro coupling | |
| —CONH$_2$ | Gln | Carbohydrate moiety | In vitro coupling | Yan and Wold, Biochemistry, 1984, Jul 31; 23(16): 3759–65 |
| Aldehyde Ketone | Oxidized oligo-saccharide | Polymer, e.g. PEG, PEG-hydrazide | PEGylation | Andresz et al., 1978, Macromol. Chem. 179: 301, WO 92/16555, WO 00/23114 |
| Guanidino | Arg | Carbohydrate moiety | In vitro coupling | Lundblad and Noyes, Chemical Reagents for Protein Modification, CRC Press Inc., Florida, USA |
| Imidazole ring | His | Carbohydrate moiety | In vitro coupling | As for guanidine |

For in vivo N-glycosylation, the term "attachment group" is used in an unconventional way to indicate the amino acid residues constituting a N-glycosylation site (with the sequence N—X—S/T/C as indicated above). Although the asparagine residue of the N-glycosylation site is the one to which the sugar moiety is attached during glycosylation, such attachment cannot be achieved unless the other amino acid residues of the N-glycosylation site are present.

Accordingly, when the non-polypeptide moiety is a sugar moiety and the conjugation is to be achieved by in vivo N-glycosylation, the term "amino acid residue comprising an attachment group for a non-polypeptide moiety" as used in connection with alterations of the amino acid sequence of the polypeptide is to be understood as meaning that one or more amino acid residues constituting an in vivo N-glycosylation site are to be altered in such a manner that a functional in vivo N-glycosylation site is introduced into the amino acid sequence.

In the present application, amino acid names and atom names (e.g. CA, CB, CD, CG, SG, NZ, N, O, C, etc) are used as defined by the Protein DataBank (PDB) (www.pdb.org) based on the IUPAC nomenclature (IUPAC Nomenclature and Symbolism for Amino Acids and Peptides (residue names, atom names, etc.), *Eur. J. Biochem.*, 138, 9-37 (1984) together with their corrections in *Eur. J. Biochem.*, 152, 1 (1985)).

The term "amino acid residue" is intended to include any natural or synthetic amino acid residue, and is primarily intended to indicate an amino acid residue contained in the group consisting of the 20 naturally occurring amino acids, i.e. selected from the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terminology used for identifying amino acid positions is illustrated as follows: G124 indicates that position 124 is occupied by a glycine residue in the amino acid sequence shown in SEQ ID NO: 1. G124R indicates that the glycine residue of position 124 has been substituted with an arginine residue. Alternative substitutions are indicated with a "/", e.g. N145S/T means an amino acid sequence in which asparagine in position 145 is substituted with either serine or threonine. Multiple substitutions are indicated with a "+", e.g. K143N+ N145S/T means an amino acid sequence which comprises a substitution of the lysine residue in position 143 with an asparagine residue and a substitution of the asparagine residue in position 145 with a serine or a threonine residue. Insertion of an additional amino acid residue, e.g. insertion of an alanine residue after G124, is indicated by G124GA. Insertion of two additional alanine residues after G124 is indicated by G124GAA, etc. When used herein, the term "inserted in position X" or "inserted at position X" means that the amino acid residue(s) is (are) inserted between amino acid residue X and X+1. A deletion of an amino acid residue is indicated by an asterix. For example, deletion of the glycine residue in position 124 is indicated by G124*.

Unless otherwise indicated, the numbering of amino acid residues made herein is made relative to the amino acid sequence of the hFVII/hFVIIa polypeptide (SEQ ID NO:1).

The term "differs from" as used in connection with specific mutations is intended to allow for additional differences being present apart from the specified amino acid difference. For instance, in addition to the modifications performed in the Gla domain aiming at increasing the FX activation, the polypeptide may contain other modifications that are not necessarily related to this effect.

Thus, in addition to the amino acid modifications disclosed herein, it will be understood that the amino acid sequence of the polypeptide variant of the invention may, if desired, contain other alterations, i.e. other substitutions, insertions or deletions. These may, for example, include truncation of the N- and/or C-terminus by one or more amino acid residues (e.g. by 1-10 amino acid residues), or addition of one or more extra residues at the N- and/or C-terminus, e.g. addition of a methionine residue at the N-terminus or introduction of a cysteine residue near or at the C-terminus, as well as "conservative amino acid substitutions", i.e. substitutions performed within groups of amino acids with similar characteristics, e.g. small amino acids, acidic amino acids, polar amino acids, basic amino acids, hydrophobic amino acids and aromatic amino acids.

Examples of such conservative substitutions are shown in the below table.

| | | | | |
|---|---|---|---|---|
| 1 | Alanine (A) | Glycine (G) | Serine (S) | Threonine (T) |
| 2 | Aspartic acid (D) | Glutamic acid (E) | | |
| 3 | Asparagine (N) | Glutamine (Q) | | |
| 4 | Arginine (R) | Histidine (H) | Lysine (K) | |
| 5 | Isoleucine (I) | Leucine (L) | Methionine (M) | Valine (V) |
| 6 | Phenylalanine (F) | Tyrosine (Y) | Tryptophan (W) | |

Still other examples of additional modifications are disclosed in the sections entitled "Modifications outside the Gla domain" and "Other modifications outside the Gla domain".

The term "nucleotide sequence" is intended to indicate a consecutive stretch of two or more nucleotide molecules. The nucleotide sequence may be of genomic, cDNA, RNA, semisynthetic, synthetic origin, or any combinations thereof.

The term "vector" refers to a plasmid or other nucleotide sequences that are capable of replicating within a host cell or being integrated into the host cell genome, and as such, are useful for performing different functions in conjunction with compatible host cells (a vector-host system) to facilitate the cloning of the nucleotide sequence, i.e. to produce useful quantities of the sequence, to direct the expression of the gene product encoded by the sequence and to integrate the nucleotide sequence into the genome of the host cell. The vector will contain different components depending upon the function it is to perform.

"Cell", "host cell", "cell line" and "cell culture" are used interchangeably herein and all such terms should be understood to include progeny resulting from growth or culturing of a cell.

"Transformation" and "transfection" are used interchangeably to refer to the process of introducing DNA into a cell.

"Operably linked" refers to the covalent joining of two or more nucleotide sequences, by means of enzymatic ligation or otherwise, in a configuration relative to one another such that the normal function of the sequences can be performed. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

In the context of the present invention the term "modification" or "amino acid modification" is intended to cover replacement of an amino acid side chain, substitution of an amino acid residue, deletion of an amino acid residue or insertion of an amino acid residue.

The term "introduce" refers to introduction of an amino acid residue, in particular by substitution of an existing amino acid residue, or alternatively by insertion of an additional amino acid residue.

The term "remove" refers to removal of an amino acid residue, in particular by substitution of the amino acid residue to be removed by another amino acid residue, or alternatively by deletion (without substitution) of the amino acid residue to be removed.

In the present context, the term "activity" should be understood as the relevant activity associated with the assay in which the activity is actually measured.

Thus, the term "amidolytic activity" is used to mean the activity measured in the "Amidolytic Assay" described herein. In order to exhibit "amidolytic activity" a variant of the invention, in its activated form, should have at least 10% of the amidolytic activity of rhFVIIa when assayed in the "Amidolytic Assay" described herein. In a preferred embodiment of the invention the variant, in its activated form, has at least 20% of the amidolytic activity of rhFVIIa, such as at least 30%, e.g. at least 40%, more preferably at least 50%, such as at least 60%, e.g. at least 70%, even more preferably at least 80%, such as at least 90% of the amidolytic activity of rhFVIIa when assayed in the "Amidolytic Assay" described herein. In an interesting embodiment the variant, in its activated form, has substantially the same amidolytic activity as rhFVIIa, such as an amidolytic activity of 75-125% of the amidolytic activity of rhFVIIa.

The term "clotting activity" refers to the activity measured in the "Whole Blood Assay" described herein, i.e. the time needed to obtain clot formation. Thus, a lower clotting time corresponds to a higher clotting activity.

The term "increased clotting activity" is used to indicate that the clotting time of the polypeptide variant is statistically significantly decreased relative to that generated by rhFVIIa or [P10Q+K32E]rhFVIIa as determined under comparable conditions and when measured in the "Whole Blood Assay" described herein.

In the present context, the term "activity" is also used in connection with the variants' capability of activating FX to FXa. This activity is also denoted "FX activation activity" or "FXa generation activity" and may be determined in the "TF-independent Factor X Activation Assay" described herein.

The term "increased FX activation activity" or "increased FXa generation activity" is used to indicate that a variant of the invention, in its activated form, has a statistically significantly increased capability to activate FX to FXa as compared to a reference molecule, such as rhFVIIa or [P10Q+K32E] rhFVIIa. To what extent a variant of the invention (in its activated form) has an increased FX activation activity may conveniently be determined in the "TF-independent Factor X Activation Assay" described herein.

The term "immunogenicity" as used in connection with a given substance is intended to indicate the ability of the substance to induce a response from the immune system. The immune response may be a cell or antibody mediated response (see, e.g., Roitt: Essential Immunology (10th Edition, Blackwell) for further definition of immunogenicity).

Normally, reduced antibody reactivity will be an indication of reduced immunogenicity. The immunogenicity may be determined by use of any suitable method known in the art, e.g. in vivo or in vitro.

The term "functional in vivo half-life" is used in its normal meaning, i.e. the time at which 50% of the biological activity of the polypeptide is still present in the body/target organ, or the time at which the activity of the polypeptide is 50% of the initial value.

As an alternative to determining functional in vivo half-life, "serum half-life" may be determined, i.e. the time at which 50% of the polypeptide circulates in the plasma or bloodstream prior to being cleared. Determination of serum half-life is often more simple than determining the functional in vivo half-life, and the magnitude of serum half-life is usually a good indication of the magnitude of functional in vivo half-life. Alternative terms to serum half-life include "plasma half-life", "circulating half-life", "serum clearance", "plasma clearance" and "clearance half-life". The polypeptide is cleared by the action of one or more of the reticuloendothelial systems (RES), kidney, spleen or liver, by tissue factor, SEC receptor or other receptor mediated elimination, or by specific or unspecific proteolysis. Normally, clearance depends on size (relative to the cutoff for glomerular filtration), charge, attached carbohydrate chains, and the presence of cellular receptors for the protein. The functionality to be retained is normally selected from procoagulant, proteolytic or receptor binding activity. The functional in vivo half-life and the serum half-life may be determined by any suitable method known in the art.

The term "increased" as used about the functional in vivo half-life or serum half-life is used to indicate that the relevant half-life of the polypeptide variant is statistically significantly increased relative to that of as reference molecule, such as rhFVIIa or [P10Q+K32E]rhFVIIa, as determined under comparable conditions (typically determined in an experimental animal, such as rats, rabbits, pigs or monkeys).

The term "$AUC_{iv}$" or "Area Under the Curve when administered intravenously" is used in its normal meaning, i.e. as the area under the activity in serum-time curve, where the polypeptide variant has been administered intravenously, in particular when administered intravenously in rats. Typically, the activity measured is the "clotting activity" as defined above. Once the experimental activity-time points have been determined, the $AUC_{iv}$ may conveniently be calculated by a computer program, such as GraphPad Prism 3.01.

It will be understood that in order to make a direct comparison between the $AUC_{iv}$-values of different molecules (e.g. between the variants of the invention and a reference molecule such as rhFVIIa or [P10Q+K32E]rhFVIIa) the same amount of activity should be administered. Consequently, the $AUC_{iv}$-values are typically normalized (i.e. corrected for differences in the injected dose) and expressed as $AUC_{iv}$/dose administered.

The term "reduced sensitivity to proteolytic degradation" is primarily intended to mean that the polypeptide variant has reduced sensitivity to proteolytic degradation in comparison to hFVIIa, rhFVIIa or [P10Q+K32E]rhFVIIa as determined under comparable conditions. Preferably, the proteolytic degradation is reduced by at least 10% (e.g. by 10-25% or by 10-50%), such as at least 25% (e.g. by 25-50%, by 25-75% or by 25-100%), more preferably by at least 35%, such as at least 50%, (e.g. by 50-75% or by 50-100%) even more preferably by at least 60%, such as by at least 75% (e.g. by 75-100%) or even at least 90%.

The term "renal clearance" is used in its normal meaning to indicate any clearance taking place by the kidneys, e.g. by glomerular filtration, tubular excretion or degradation in the tubular cells. Renal clearance depends on physical characteristics of the polypeptide, including size (diameter), hydrodynamic volume, symmetry, shape/rigidity, and charge. Normally, a molecular weight of about 67 kDa is considered to be a cut-off-value for renal clearance. Renal clearance may be established by any suitable assay, e.g. an established in vivo assay. Typically, renal clearance is determined by administering a labelled (e.g. radiolabelled or fluorescence labelled) polypeptide to a patient and measuring the label activity in urine collected from the patient. Reduced renal clearance is determined relative to a corresponding reference polypeptide, e.g. rhFVIIa or [P10Q+K32E]rhFVIIa, under comparable conditions. Preferably, the renal clearance rate of the polypeptide variant is reduced by at least 50%, preferably by at least 75%, and most preferably by at least 90% compared to rhFVIIa or [P10Q+K32E]rhFVIIa.

The terms "tissue factor binding site", "active site region" and "ridge of the active site binding cleft" are defined with reference to Example 1.

The term "hydrophobic amino acid residue" includes the following amino acid residues: Isoleucine (I), leucine (L), methionine (M), valine (V), phenylalanine (F), tyrosine (Y) and tryptophan (W).

The term "negatively charged amino acid residue" includes the following amino acid residues: Aspartic acid (D) and glutamic acid (E).

The term "positively charged amino acid residue" includes the following amino acid residues: Lysine (K), arginine (R) and histidine (H).

Variants of the Invention

The modifications performed in the Gla domain of the parent polypeptide preferably provide the resulting molecule with an increased phospholipid membrane binding affinity, an improved capability to activate FX to Fxa, and/or an increased clotting activity. The variants of the invention may also have a reduced tissue factor binding affinity and a reduced activity when bound to tissue factor.

Without being limited by any particular theory, it is presently believed that enhanced phospholipid membrane binding affinity results in a higher local concentration of the activated polypeptide variants in close proximity to the other coagulation factors, particularly FX. Thus, the rate of activation of FX to FXa will be higher, simply due to a higher molar ratio of the activated FVII variant to FX. The increased activation rate of FX then results in a higher amount of active thrombin, and thus a higher rate of cross-linking of fibrin.

Consequently, it is contemplated that medical treatment with a polypeptide variant according to the invention may provide advantages over the currently available rhFVIIa compound (NovoSeven®), such as a lower dose, increased efficacy and/or faster action.

Further, it is believed that tissue factor-independent variants, i.e. variants that have a reduced activity when bound to tissue factor compared to wild-type human Factor VIIa, may offer certain safety advantages in terms of reduced risk of undesired blood clot formation (e.g. thrombosis or thromboembolism), in particular when used for treatment of acute uncontrolled bleeding events such as trauma, including traumatic brain injury, or intracerebral haemorrhage.

Thus, in a highly preferred embodiment of the invention, the polypeptide variant, in its activated form and when compared to a reference molecule, such as rhFVIIa or [P10Q+ K32E]rhFVIIa, has an increased FX activation activity, in particular when assayed in a tissue factor-independent assay, such as the "TF-independent Factor X Activation Assay" disclosed herein. More particularly, it is preferred that the ratio between the FX activation activity of the polypeptide variant, in its activated form, and the FX activation activity of a reference molecule is at least 1.25 when assayed in the "TF-independent Factor X Activation Assay" disclosed herein. More preferably, this ratio is at least 1.5, such as at least 1.75, e.g. at least 2, even more preferably at least 3, such as at least 4, most preferably at least 5.

When the reference molecule is rhFVIIa, the ratio between the FX activation activity of the polypeptide variant, in its activated form, and the FX activation activity of rhFVIIa is preferably at least about 5, typically at least about 10, when assayed in the "TF-independent Factor X Activation Assay" disclosed herein, such as at least about 15 or 20.

In another highly preferred embodiment of the invention, the variants of the invention possess an increased clotting activity (i.e. a reduced clotting time) as compared to rhFVIIa or [P10Q+K32E]rhFVIIa. In a preferred embodiment of the invention the ratio between the time to reach clot formation for the variant ($t_{variant}$) and the time to reach clot formation for rhFVIIa ($t_{wt}$) or [P10Q+K32E]rhFVIIa ($t_{P10Q+K32E}$) is at the most 0.9 when assayed in the "Whole Blood Assay" described herein. More preferably this ratio is at the most 0.75, such as 0.7, even more preferably the ratio is at the most 0.6, and most preferably the ratio is at the most 0.5.

One or more of the above-mentioned properties may be achieved by the modifications described herein.

Variants of the Invention Comprising a Hydrophobic Amino Acid Residue in Position 34

As indicated above, the present invention relates in a first aspect to a FVII or FVIIa polypeptide variant having an amino acid sequence comprising 1-15 amino acid modifications relative to hFVII or hFVIIa (SEQ ID NO:1), wherein a hydrophobic amino acid residue has been introduced by substitution in position 34.

The hydrophobic amino acid residue to be introduced in position 34 may be selected from the group consisting of I, L, M, V, F, Y and W, preferably I, L and V, in particular L.

In a preferred embodiment, the variant further comprises an amino acid substitution in position 10, in particular P10Q, and/or an amino acid substitution in position 32, in particular K32E. In a particular preferred embodiment of the invention, the variant comprises substitutions in both of positions 10 and 32, such as P10Q+K32E.

Accordingly, in an interesting embodiment of the invention, the variant comprises the substitutions P10Q+K32E+A34L.

In a particular interesting embodiment of the invention, the variant further comprises an insertion of at least one (typically one) amino acid residue between position 3 and 4. It is preferred that the inserted amino acid residue is a hydrophobic amino acid residue. Most preferably the insertion is A3AY. Accordingly, in a particular interesting embodiment of the invention, the variant comprises the modifications A3AY+P10Q+K32E+A34L.

In addition to any of the above-mentioned modifications, the variant may comprise a further substitution in position 33. Preferably, a hydrophobic amino acid residue is introduced by substitution in position 33, in particular D33F.

The Gla domain may also contain modifications in other positions, in particular in positions 8, 11 and 28, such as R28F or R28E. On the other hand it should be understood that the Gla domain should not be modified to such an extent that the membrane binding properties are impaired. Accordingly, it is preferred that no modifications are made in the residues that become γ-carboxylated, i.e. it is preferred that no modifications are made in residues 6, 7, 14, 16, 19, 20, 25, 26, 29 and 35. In a similar way, it is in general not preferred that non-polypeptide moieties, such as sugar moieties and/or PEG groups, are introduced in the Gla domain. Consequently, it is preferred that no modifications are made in the Gla domain that create an in vivo N-glycosylation site.

Finally, it will be understood that the modifications in the Gla domain discussed in this section may advantageously be combined with one or more modifications in positions located outside the Gla domain (see the sections entitled "Modifications outside the Gla domain" and "Other modifications outside the Gla domain" below).

Variants of the Invention Comprising an Amino Acid Substitution in Position 36

As indicated above, the invention relates in a second aspect to a FVII or FVIIa polypeptide variant having an amino acid sequence comprising 1-15 amino acid modifications relative to hFVII or hFVIIa (SEQ ID NO:1), wherein said amino acid sequence comprises an amino acid substitution in position 36.

Preferably, the amino acid residue to be introduced by substitution in position 36 is a negatively charged amino acid residue, e.g. R36E or R36D, in particular R36E.

In a preferred embodiment, the variant further comprises an amino acid substitution in position 10, in particular P10Q, and/or an amino acid substitution in position 32, in particular K32E. In a particular preferred embodiment of the invention, the variant comprises substitutions in both of positions 10 and 32, such as P10Q+K32E.

The variant of the invention may further contain a substitution in position 38. It is preferred that a negatively charged amino acid residue is introduced by substitution in position 38, e.g. K38E or K38D, in particular K38E.

Accordingly, interesting variants are those that comprise the following substitutions P10Q+K32E+R36E or P10Q+K32E+R36E+K38E.

In a particular interesting embodiment, the variant further comprises an amino acid substitution in position 34 (i.e. the resulting variant comprises substitutions in the following residues 10+32+34+36 or 10+32+34+36+38). Preferably, a negatively charged amino acid residue is introduced by substitution in position 34, e.g. A34E or A34D.

Specific examples of preferred variants are those that comprise the following substitutions P10Q+K32E+A34E+R36E or P10Q+K32E+A34D+R36E+K38E.

In an interesting embodiment of the invention, the variant further comprises an insertion of at least one (typically one) amino acid residue between position 3 and 4. It is preferred that the inserted amino acid residue is a hydrophobic amino acid residue. Most preferably the insertion is A3AY.

In addition to any of the above-mentioned modifications, the variant may comprise a further substitution in position 33. Preferably, a hydrophobic amino acid residue is introduced by substitution in position 33, in particular D33F.

The Gla domain may also contain modifications in other positions, in particular in positions 8, 11 and 28, such as R28F or R28E. On the other hand it should be understood that the Gla domain should not be modified to such an extent that the membrane binding properties are impaired. Accordingly, it is preferred that no modifications are made in the residues that become γ-carboxylated, i.e. it is preferred that no modifications are made in residues 6, 7, 14, 16, 19, 20, 25, 26, 29 and 35. In a similar way, it is in general not preferred that non-polypeptide moieties, such as sugar moieties and/or PEG groups, are introduced in the Gla domain. Consequently, it is preferred that no modifications are made in the Gla domain that create an in vivo N-glycosylation site.

Finally, it will be understood that the modifications in the Gla domain discussed in this section may advantageously be combined with one or more modifications in positions located outside the Gla domain (see the sections entitled "Modifications outside the Gla domain" and "Other modifications outside the Gla domain" below).

Variants of the Invention Comprising Amino Acid Substitutions in Positions 74, 77 or 116

As indicated above, the present invention relates in a third aspect to a FVII or FVIIa polypeptide variant having an amino acid sequence comprising 3-15 amino acid modifications relative to hFVII or hFVIIa (SEQ ID NO:1), wherein said amino acid sequence comprises an amino acid substitution in position 10, 32 and at least one further amino acid substitution in a position selected from the group consisting of position 74, 77 and 116.

In a preferred embodiment, the amino acid substitution in position 10 is P10Q and the amino acid substitution in position 32 is K32E It is further preferred that the substitution in position 74, 77 or 116 is selected from the group consisting of P74S, E77A and E116D.

In an interesting embodiment the variant further comprises an amino acid substitution in position 34. Preferably, a negatively charged amino acid residue is introduced by substitution in position 34, e.g. A34E or A34D, in particular A34E.

In another interesting embodiment of the invention the variant further comprises an insertion of at least one (typically one) amino acid residue between position 3 and 4. It is preferred that the inserted amino acid residue is a hydrophobic amino acid residue. Most preferably the insertion is A3AY.

Thus, specific examples of interesting variants include variants comprising the following modifications A3AY+P10Q+K32E+E116D, A3AY+P10Q+K32E+E77A and P10Q+K32E+A34E+P74S.

In addition to any of the above-mentioned modifications, the variant may comprise a further substitution in position 33. Preferably, a hydrophobic amino acid residue is introduced by substitution in position 33, in particular D33F.

The Gla domain may also contain modifications in other positions, in particular in positions 8, 11 and 28, such as R28F or R28E. As explained above, the Gla domain should not be modified to such an extent that the membrane binding properties are impaired, i.e. preferably no modifications are made in residues 6, 7, 14, 16, 19, 20, 25, 26, 29 and 35, and it is preferred that an in vivo N-glycosylation site is not created in the Gla domain.

Finally, it will be understood that the modifications in the Gla domain discussed in this section may advantageously be combined with one or more modifications in positions located outside the Gla domain (see the sections entitled "Modifications outside the Gla domain" and "Other Modifications Outside the Gla Domain" below).

Modifications Outside the Gla Domain

A circulating rhFVIIa half-life of 2.3 hours was reported in "Summary Basis for Approval for NovoSeven®", FDA reference number 96-0597. Relatively high doses and frequent administration are necessary to reach and sustain the desired therapeutic or prophylactic effect. As a consequence, adequate dose regulation is difficult to obtain and the need for frequent intravenous administration imposes restrictions on the patient's way of living.

A molecule with a longer circulation half-life and/or increased bioavailability (such as an increased Area Under the Curve as compared to rhFVIIa when administered intravenously) would decrease the number of necessary administrations. Given the current need for frequent injections and the potential for obtaining more optimal therapeutic FVIIa levels with concomitant enhanced therapeutic effect, there is a clear need for improved FVII- or FVIIa-like molecules.

Accordingly, a further object of the present invention is to provide improved FVII or FVII molecules (FVII or FVIIa variants) with an increased bioavailability (such as an increased Area Under the Curve as compared to a reference molecule, such as rhFVIIa or [P10Q+K32E]rhFVIIa, when administered intravenously) and which are capable of activating factor X to factor Xa (without binding to tissue factor) more efficiently than a reference molecule, such as rhFVIIa or [P10Q+K32E]rhFVIIa (thereby being able to treat uncontrolled bleadings, such as a trauma, or chronic conditions such as hemophilia more efficiently).

Thus, interesting variants of the invention are those which, in their activated forms and when compared to a reference molecule, such as rhFVIIa or [P10Q+K32E]rhFVIIa, generate an increased Area Under the Curve when administered intravenously ($AUC_{iv}$). This can conveniently be determined by intravenous administration in rats. More particularly, interesting variants of the present invention are those where the ratio between the $AUC_{iv}$ of said variant, in its actvated form, and the $AUC_{iv}$ of a reference molecule, such as rhFVIIa or [P10Q+K32E]rhFVIIa, is at least 1.25, such as at least 1.5, e.g. at least 1.75, more preferably at least 2, such as at least 3, even more preferably at least 4, such as at least 5, in particular when administered (intravenously) in rats.

This effect will often correspond to an increased functional in vivo half-life and/or an increased serum half-life as compared to a reference molecule, such as rhFVIIa or [P10Q+K32E]rhFVIIa. Accordingly, in another interesting embodiment of the invention, the ratio between the functional in vivo half-life or the serum half-life for the variant, in its activated form, and the functional in vivo half-life or the serum half-life for a reference molecule, such as rhFVIIa or [P10Q+K32E]rhFVIIa, is at least 1.25. More preferably, the ratio between the relevant half-life for the variant, in its activated form, and the relevant half-life for the reference molecule, such as rhFVIIa or [P10Q+K32E]rhFVIIa, is at least 1.5, such as at least 1.75, e.g. at least 2, even more preferably at least 3, such as at least 4, e.g. at least 5.

One way to increase the circulation half-life of a protein is to ensure that renal clearance of the protein is reduced. This may be achieved by conjugating the protein to a chemical moiety which is capable of conferring reduced renal clearance to the protein, e.g. polyethylene glycol (PEG).

Furthermore, attachment of a chemical moiety to the protein or substitution of amino acids exposed to proteolysis may effectively block a proteolytic enzyme from contact that otherwise leads to proteolytic degradation of the protein.

As indicated above, instability due to proteolytic degradation is a known problem in current rhFVIIa treatment. Proteolytic degradation is thus a major obstacle for obtaining a preparation in solution as opposed to a lyophilized product. The advantage of obtaining a stable soluble preparation lies in easier handling for the patient, and, in the case of emergencies, quicker action, which potentially can become life saving. Attempts to prevent proteolytic degradation by site directed mutagenesis at major proteolytic sites have been disclosed in WO 88/10295.

WO 01/58935 discloses a number of suitable modifications leading to an increase in $AUC_{iv}$, functional in vivo half-life and/or serum half-life. The variants disclosed in WO 01/58935 are the result of a generally new strategy for developing improved FVII or FVIIa molecules, which may also be used for the parent FVII or FVIIa polypeptide of the present invention.

More specifically, by removing and/or introducing an amino acid residue comprising an attachment group for a non-polypeptide moiety in the parent FVII or FVIIa polypeptide it is possible to specifically adapt the polypeptide so as to make the molecule more susceptible to conjugation to a non-polypeptide moiety of choice, to optimize the conjugation pattern (e.g. to ensure an optimal distribution and number of non-polypeptide moieties on the surface of the FVII or FVIIa polypeptide variant and to ensure that only the attachment groups intended to be conjugated is present in the molecule) and thereby obtain a new conjugate molecule which has amidolytic activity and in addition one or more improved properties as compared to rhFVIIa In interesting embodiments of the present invention more than one amino acid residue located outside the Gla domain is altered, e.g. the alteration embraces removal as well as introduction of amino acid residues comprising an attachment group for the non-polypeptide moiety of choice. In addition to the removal and/or introduction of amino acid residues the polypeptide variant may comprise other substitutions that are not related to introduction and/or removal of amino acid residues comprising an attachment group for the non-polypeptide moiety.

Also, the polypeptide variant may be attached to a serine proteinase inhibitor to inhibit the catalytic site of the polypeptide variant. Alternatively, one or more of the amino acid residues present in the catalytic site (S344, D242 and H193) may be mutated in order to render the resulting variant inactive. One example of such a mutation is S344A.

The amino acid residue comprising an attachment group for a non-polypeptide moiety, whether it be removed or introduced, is selected on the basis of the nature of the non-polypeptide moiety of choice and, in most instances, on the basis of the method in which conjugation between the polypeptide variant and the non-polypeptide moiety is to be achieved. For instance, when the non-polypeptide moiety is a polymer molecule such as a polyethylene glycol or polyalkylene oxide derived molecule, amino acid residues comprising an attachment group may be selected from the group consisting of lysine, cysteine, aspartic acid, glutamic acid, histidine, and tyrosine, preferably lysine, cysteine, aspartic acid and glutamic acid, more preferably lysine and cysteine, in particular cysteine.

Whenever an attachment group for a non-polypeptide moiety is to be introduced into or removed from the parent polypeptide, the position of the amino acid residue to be modified is preferably located at the surface of the parent FVII or FVIIa polypeptide, and more preferably occupied by an amino acid residue which has at least 25% of its side chain exposed to the surface (as defined in Example 1 herein), preferably at least 50% of its side chain exposed to the surface (as defined in Example 1 herein). Such positions have been identified on the basis of an analysis of a 3D structure of the hFVII or hFVIIa molecule as described in WO 01/58935.

Furthermore, the position to be modified is preferably selected from a part of the FVII or FVIIa molecule that is located outside the tissue factor binding site, and/or outside the active site region, and/or outside the ridge of the active site binding cleft. These sites/regions are identified in Example 1 herein and in WO 01/58935.

In case of removal of an attachment group, the relevant amino acid residue comprising such group and occupying a position as defined above is preferably substituted with a different amino acid residue that does not comprise an attachment group for the non-polypeptide moiety in question. Normally, the amino acid residue to be removed is one to which conjugation is disadvantageous, e.g. an amino acid residue located at or near a functional site of the polypeptide (since conjugation at such a site may result in inactivation or reduced activity of the resulting conjugate due to, e.g., impaired receptor recognition). In the present context the term "functional site" is intended to indicate one or more amino acid residues which is/are essential for or otherwise involved in the function or performance of FVII or FVIIa. Such amino acid residues are a part of the functional site. The functional site may be determined by methods known in the art and is preferably identified by analysis of a structure of the FVIIa-tissue factor complex (See Banner et al., *Nature* 1996; 380:41-46).

In case of introduction of an attachment group, an amino acid residue comprising such group is introduced into the relevant position, preferably by substitution of the amino acid residue occupying such position.

The exact number of attachment groups present and available for conjugation in the FVII or FVIIa polypeptide is dependent on the effect desired to be achieved by the conjugation. The effect to be obtained is, e.g., dependent on the nature and degree of conjugation (e.g. the identity of the non-polypeptide moiety, the number of non-polypeptide moieties desirable or possible to conjugate to the polypeptide variant, where they should be conjugated or where conjugation should be avoided, etc.).

The total number of amino acid residues to be modified outside the Gla domain in the parent FVII or FVIIa polypeptide (as compared to the amino acid sequence shown in SEQ ID NO:1) will typically not exceed 10. Preferably, the FVII or FVIIa variant comprises an amino acid sequence which differs in 1-10 amino acid residues from amino acid residues 46-406 shown in SEQ ID NO:1, typically in 1-8 or in 2-8 amino acid residues, e.g. in 1-5 or in 2-5 amino acid residues, such as in 1-4 or in 1-3 amino acid residues, e.g. in 1, 2 or 3 amino acid residues from amino acid residues 46-406 shown in SEQ ID NO:1.

Analogously, the polypeptide variant of the invention may contain 1-10 (additional) non-polypeptide moieties, typically 1-8 or 2-8 (additional) non-polypeptide moieties, preferably 1-5 or 2-5 (additional) non-polypeptide moieties, such as 1-4 or 1-3 (additional) non-polypeptide moieties, e.g. 1, 2 or 3 (additional) non-polypeptide moieties. It will be understood that such additional non-polypeptide moieties are covalently attached to an attachment group located outside the Gla domain.

Polypeptide Variants of the Invention Where the Non-Polypeptide Moiety is a Sugar Moiety In a preferred embodiment of the invention, an attachment group for a sugar moiety, such as a glycosylation site, in particular an in vivo glycosylation site, such as an in vivo N-glycosylation site, has been introduced and/or removed, preferably introduced, in a position located outside the Gla domain.

When used in the present context, the term "naturally occurring glycosylation site" covers the glycosylation sites at positions N145, N322, S52 and S60. The term "naturally occurring in vivo O-glycosylation site" includes the positions S52 and S60, whereas the term "naturally occurring in vivo N-glycosylation site" includes positions N145 and N322.

Thus, in a very interesting embodiment of the invention, the non-polypeptide moiety is a sugar moiety and the introduced attachment group is a glycosylation site, preferably an in vivo glycosylation site, such as an in vivo O-glycosylation site or an in vivo N-glycosylation site, in particular an in vivo N-glycosylation site. Typically, 1-10 glycosylation sites, in particular in vivo N-glycosylation sites, have been introduced, preferably 1-8, 1-6, 1-4 or 1-3 glycosylation sites, in particular in vivo N-glycosylation sites, have been introduced in one or more positionss located outside the Gla domain. For example 1, 2 or 3 glycosylation sites, in particular in vivo N-glycosylation sites, may have been introduced outside the Gla domain, preferably by substitution.

It will be understood that in order to prepare a polypeptide variant wherein the polypeptide variant comprises one or more glycosylation sites, the polypeptide variant must be expressed in a host cell capable of attaching sugar (oligosaccharide) moieties at the glycosylation site(s) or alternatively subjected to in vitro glycosylation. Examples of glycosylating host cells are given in the section further below entitled "Coupling to a sugar moiety".

Examples of positions wherein the glycosylation sites, in particular in vivo N-glycosylation sites, may be introduced include amino acid residues having at least 25% of their side chain exposed to the surface (as defined in Example 1 herein), such as at least 50% of the side chain exposed to the surface. The position is preferably selected from a part of the molecule that is located outside the tissue factor binding site and/or the active site region and/or outside the ridge of the active site cleft, as defined in Example 1 herein. It should be understood that when the term "at least 25% (or at least 50%) of its side chain exposed to the surface" is used in connection with introduction of an in vivo N-glycosylation site this term refers to the surface accessibility of the amino acid side chain in the position where the sugar moiety is actually attached. In many cases it will be necessary to introduce a serine or a threonine residue in position +2 relative to the asparagine residue to which the sugar moiety is actually attached, and these positions where the serine or threonine residues are introduced are allowed to be buried, i.e. to have less than 25% of their side chains exposed to the surface.

Specific and preferred examples of such substitutions creating an in vivo N-glycosylation site include a substitution selected from the group consisting of A51N, G58N, T106N, K109N, G124N, K143N+N145T, A175T, I205S, I205T, V253N, T267N, T267N+S269T, S314N+K316S, S314N+K316T, R315N+V317S, R315N+V317T, K316N+G318S, K316N+G318T, G318N, D334N and combinations thereof. More preferably, the in vivo N-glycosylation site is introduced by a substitution selected from the group consisting of A51N, G58N, T106N, K109N, G124N, K143N+N145T, A175T, I205T, V253N, T267N+S269T, S314N+K316T, R315N+V317T, K316N+G318T, G318N, D334N and combinations thereof. Even more preferably, the in vivo N-glycosylation site is introduced by a substitution selected from the group consisting of T106N, A175T, I205T, V253N, T267N+S269T and combinations thereof, in particular one, two or three of T106N, I205T and V253N.

In one embodiment, only one in vivo N-glycosylation site has been introduced by substitution. In another embodiment, two or more (such as two) in vivo N-glycosylation sites have been introduced by substitution. Examples of preferred substitutions creating two in vivo N-glycosylation sites include substitutions selected from the group consisting of A51N+G58N, A51N+T106N, A51N+K109N, A51N+G124N, A51N+K143N+N145T, A51N+A175T, A51N+I205T, A51N+V253N, A51N+T267N+S269T, A51N+S314N+K316T, A51N+R315N+V317T, A51N+K316N+G318T, A51N+G318N, A51N+D334N, G58N+T106N, G58N+K109N, G58N+G124N, G58N+K143N+N145T, G58N+A175T, G58N+I205T, G58N+V253N, G58N+T267N+S269T, G58N+S314N+K316T, G58N+R315N+V317T, G58N+K316N+G318T, G58N+G318N, G58N+D334N, T106N+K109N, T106N+G124N, T106N+K143N+N145T, T106N+A175T, T106N+I205T, T106N+V253N, T106N+T267N+S269T, T106N+S314N+K316T, T106N+R315N+V317T, T106N+K316N+G318T, T106N+G318N, T106N+D334N, K109N+G124N, K109N+K143N+N145T, K109N+A175T, K109N+I205T, K109N+V253N, K109N+T267N+S269T, K109N+S314N+K316T, K109N+R315N+V317T, K109N+K316N+G318T, K109N+G318N, K109N+D334N, G124N+K143N+N145T, G124N+A175T, G124N+I205T, G124N+V253N, G124N+T267N+S269T, G124N+S314N+K316T, G124N+R315N+V317T, G124N+K316N+G318T, G124N+G318N, G124N+D334N, K143N+N145T+A175T, K143N+N145T+I205T, K143N+N145T+V253N, K143N+N145T+T267N+S269T, K143N+N145T+S314N+K316T, K143N+N145T+R315N+V317T, K143N+N145T+K316N+G318T, K143N+N145T+G318N, K143N+N145T+D334N, A175T+I205T, A175T+V253N, A175T+T267N+S269T, A175T+S314N+K316T, A175T+R315N+V317T, A175T+K316N+G318T, A175T+G318N, A175T+D334N, I205T+V253N, I205T+T267N+S269T, I205T+S314N+K316T, I205T+R315N+V317T, I205T+K316N+G318T, I205T+G318N, I205T+D334N, V253N+T267N+S269T, V253N+S314N+K316T, V253N+R315N+V317T, V253N+K316N+G318T, V253N+G318N, V253N+D334N, T267N+S269T+S314N+K316T, T267N+S269T+R315N+V317T, T267N+S269T+K316N+G318T, T267N+S269T+G318N, T267N+S269T+D334N, S314N+K316T+R315N+V317T, S314N+K316T+G318N, S314N+K316T+D334N, R315N+V317T+K316N+G318T, R315N+V317T+G318N, R315N+V317T+D334N and G318N+D334N. More preferably, the substitutions are selected from the group consisting of T106N+A175T, T106N+I205T, T106N+V253N, T106N+T267N+S269T, A175T+I205T, A175T+V253N, A175T+T267N+S269T, I205T+V253N, I205T+T267N+S269T and V253N+T267N+S269T, even more preferably from the group consisting of T106N+I205T, T106N+V253N and I205T+V253N.

In a further embodiment, three or more (such as three) in vivo N-glycosylation sites have been introduced by substitution. Examples of preferred substitutions creating three in vivo N-glycosylation sites include substitutions selected from the group consisting of I205T+V253N+T267N+S269T and T106N+I205T+V253N.

As discussed above, it is preferred that the in vivo N-glycosylation site is introduced in a position which does not form part of the tissue factor binding site, the active site region or the ridge of the active site binding cleft as defined herein.

It will be understood that any of the modifications mentioned in the above sections may be combined with each other, in addition to being combined with the above-described substitutions in position 34 and/or 36, in particular A34E/L and/or R36E, and preferably in combination with the above-described substitutions in position 10 and/or 32, in particular P10Q and/or K32E. Among the above-identified modifications for introduction of an in vivo N-glycosylation site, preferred modifications include one, two or three of T106N, I205T and V253N, in particular two of these modifications, i.e. T106N+I205T, T106N+V253N or I205T+V253N.

Thus, in one preferred embodiment of the invention the FVII or FVIIa variant comprises the modifications P10Q+K32E+A34E+R36E+T106N+I205T.

In a further preferred embodiment the FVII or FVIIa variant comprises the modifications P10Q+K32E+A34E+R36E+T106N+V253N.

In a further preferred embodiment the FVII or FVIIa variant comprises the modifications P10Q+K32E+A34E+R36E+I205T+V253N.

In a further preferred embodiment the FVII or FVIIa variant comprises the modifications P10Q+K32E+A34L+T106N+I205T.

In a further preferred embodiment the FVII or FVIIa variant comprises the modifications P10Q+K32E+A34L+ T106N+V253N.

In a further preferred embodiment the FVII or FVIIa variant comprises the modifications P10Q+K32E+A34L+ I205T+V253N.

In a further preferred embodiment the FVII or FVIIa variant comprises the modifications P10Q+K32E+A34L+R36E+ T106N+I205T.

In a further preferred embodiment the FVII or FVIIa variant comprises the modifications P10Q+K32E+A34L+R36E+ T106N+V253N.

In a further preferred embodiment the FVII or FVIIa variant comprises the modifications P10Q+K32E+A34L+R36E+ I205T+V253N.

As is also explained above, any one or more of these modifications may in addition be combined with insertion of at least one amino acid residue, typically a single amino acid residue, between position 3 and 4, where the inserted residue is preferably a hydrophobic amino acid residue. Most preferably the insertion is A3AY. Thus, in additional preferred embodiments of the invention the FVII or FVIIa variant comprises modifications selected from:

A3AY+P10Q+K32E+A34E+R36E+T106N+I205T;
A3AY+P10Q+K32E+A34E+R36E+T106N+V253N;
A3AY+P10Q+K32E+A34E+R36E+I205T+V253N;
A3AY+P10Q+K32E+A34L+T106N+I205T;
A3AY+P10Q+K32E+A34L+T106N+V253N;
A3AY+P10Q+K32E+A34L+I205T+V253N;
A3AY+P10Q+K32E+A34L+R36E+T106N+I205T;
A3AY+P10Q+K32E+A34L+R36E+T106N+V253N;
A3AY+P10Q+K32E+A34L+R36E+I205T+V253N.

Other Modifications Outside the Gla Domain

In a further embodiment of the present invention, the FVII or FVIIa variant may, in addition to the modifications described in the sections above, also contain mutations which are already known to increase the intrinsic activity of the polypeptide, for example those described in WO 02/22776.

For example, the variant may comprise at least one modification in a position selected from the group consisting of 157, 158, 296, 298, 305, 334, 336, 337 and 374. Examples of preferred substitutions include substitutions selected from the group consisting of V158D, E296D, M298Q, L305V and K337A. More preferably, said substitutions are selected from the group consisting of V158D+E296D+M298Q+L305V+ K337A, V158D+E296D+M298Q+K337A, V158D+E296D+ M298Q+L305V, V158D+E296D+M298Q, M298Q, L305V+ K337A, L305V and K337A.

In a further embodiment of the present invention, the FVII or FVIIa variant may, in addition to the modifications described in the sections above, also contain other mutations, such as the substitution K341Q disclosed by Neuenschwander et al, *Biochemistry*, 1995; 34:8701-8707. Other possible additional substitutions include D196K, D196N, G237L, G237GAA and combinations thereof.

Additional detailed information on conjugation of FVII and FVIIa variants to non-polypeptide moieties is found in WO 01/58935 and WO 03/093465, to which reference is made and which are incorporated herein by reference.

Methods of Preparing a Conjugated Variant of the Invention

In general, a conjugated variant according to the invention may be produced by culturing an appropriate host cell under conditions conducive for the expression of the variant polypeptide, and recovering the variant polypeptide, wherein a) the variant polypeptide comprises at least one N- or O-glycosylation site and the host cell is an eukaryotic host cell capable of in vivo glycosylation, and/or b) the variant polypeptide is subjected to conjugation to a non-polypeptide moiety in vitro.

Conjugation to a Polymer Molecule

The polymer molecule to be coupled to the variant polypeptide may be any suitable polymer molecule, such as a natural or synthetic homo-polymer or hetero-polymer, typically with a molecular weight in the range of about 300-100,000 Da, such as about 500-20,000 Da, more preferably in the range of about 500-15,000 Da, even more preferably in the range of about 2-12 kDa, such as in the range of about 3-10 kDa. When the term "about" is used herein in connection with a certain molecular weight, the word "about" indicates an approximate average molecular weight and reflects the fact that there will normally be a certain molecular weight distribution in a given polymer preparation.

Examples of homo-polymers include a polyol (i.e. poly-OH), a polyamine (i.e. poly-NH$_2$) and a polycarboxylic acid (i.e. poly-COOH). A hetero-polymer is a polymer comprising different coupling groups, such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), poly-carboxylate, poly-(vinylpyrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, water soluble, and are easily excreted from living organisms.

PEG is the preferred polymer molecule, since it has only few reactive groups capable of cross-linking compared to, e.g., polysaccharides such as dextran. In particular, monofunctional PEG, e.g. methoxypolyethylene glycol (mPEG), is of interest since its coupling chemistry is relatively simple (only one reactive group is available for conjugating with attachment groups on the polypeptide). Consequently, as the risk of cross-linking is eliminated, the resulting conjugated variants are more homogeneous and the reaction of the polymer molecules with the variant polypeptide is easier to control.

To effect covalent attachment of the polymer molecule(s) to the variant polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl propionate (SPA), succinimidyl butyrate (SBA), succinimidyl carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g. from Nektar Therapeutics, Huntsville, Ala., USA, or from PolyMASC Pharmaceuticals plc, UK.

Specific examples of activated linear or branched polymer molecules for use in the present invention are described in the Nektar Molecule Engineering Catalog 2003 (Nektar Therapeutics), incorporated herein by reference.

Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. No. 5,932,462 and U.S. Pat. No. 5,643,575, both of which are incorporated herein by reference. Additional publications disclosing useful polymer molecules, PEGylation chemistries and conjugation methods are listed in WO 01/58935 and WO 03/093465.

Specific examples of activated PEG polymers particularly preferred for coupling to cysteine residues, include the following linear PEGs: vinylsulfone-PEG (VS-PEG), preferably vinylsulfone-mPEG (VS-mPEG); maleimide-PEG (MAL-PEG), preferably maleimide-mPEG (MAL-mPEG) and orthopyridyl-disulfide-PEG (OPSS-PEG), preferably orthopyridyl-disulfide-mPEG (OPSS-mPEG). Typically, such PEG or mPEG polymers will have a size of about 5 kDa, about 10 kD, about 12 kDa or about 20 kDa.

The skilled person will be aware that the activation method and/or conjugation chemistry to be used depends on the attachment group(s) of the variant polypeptide (examples of which are given further above), as well as the functional groups of the polymer (e.g. being amine, hydroxyl, carboxyl, aldehyde, sulfydryl, succinimidyl, maleimide, vinysulfone or haloacetate). The PEGylation may be directed towards conjugation to all available attachment groups on the variant polypeptide (i.e. such attachment groups that are exposed at the surface of the polypeptide) or may be directed towards one or more specific attachment groups, e.g. the N-terminal amino group as described in U.S. Pat. No. 5,985,265 or to cysteine residues. Furthermore, the conjugation may be achieved in one step or in a stepwise manner (e.g. as described in WO 99/55377).

For PEGylation to cysteine residues (see above) the FVII or FVIIa variant is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to 16 hours.

It will be understood that the PEGylation is designed so as to produce the optimal molecule with respect to the number of PEG molecules attached, the size and form of such molecules (e.g. whether they are linear or branched), and the attachment site(s) in the variant polypeptide. The molecular weight of the polymer to be used may e.g. be chosen on the basis of the desired effect to be achieved.

In connection with conjugation to only a single attachment group on the protein (e.g. the N-terminal amino group), it may be advantageous that the polymer molecule, which may be linear or branched, has a high molecular weight, preferably about 10-25 kDa, such as about 15-25 kDa, e.g. about 20 kDa.

Normally, the polymer conjugation is performed under conditions aimed at reacting as many of the available polymer attachment groups as possible with polymer molecules. This is achieved by means of a suitable molar excess of the polymer relative to the polypeptide. Typically, the molar ratios of activated polymer molecules to polypeptide are up to about 1000-1, such as up to about 200-1, or up to about 100-1. In some cases the ration may be somewhat lower, however, such as up to about 50-1, 10-1, 5-1, 2-1 or 1-1 in order to obtain optimal reaction.

It is also contemplated according to the invention to couple the polymer molecules to the polypeptide through a linker. Suitable linkers are well known to the skilled person; see also WO 01/58935.

Subsequent to the conjugation, residual activated polymer molecules are blocked according to methods known in the art, e.g. by addition of primary amine to the reaction mixture, and the resulting inactivated polymer molecules are removed by a suitable method.

It will be understood that depending on the circumstances, e.g. the amino acid sequence of the variant polypeptide, the nature of the activated PEG compound being used and the specific PEGylation conditions, including the molar ratio of PEG to polypeptide, varying degrees of PEGylation may be obtained, with a higher degree of PEGylation generally being obtained with a higher ratio of PEG to variant polypeptide. The PEGylated variant polypeptides resulting from any given PEGylation process will, however, normally comprise a stochastic distribution of conjugated polypeptide variants having slightly different degrees of PEGylation.

Coupling to a Sugar Moiety

In order to achieve in vivo glycosylation of a FVII molecule comprising one or more glycosylation sites the nucleotide sequence encoding the variant polypeptide must be inserted in a glycosylating, eucaryotic expression host. The expression host cell may be selected from fungal (filamentous fungal or yeast), insect or animal cells or from transgenic plant cells. In one embodiment the host cell is a mammalian cell, such as a CHO cell, BHK or HEK, e.g. HEK 293, cell, or an insect cell, such as an SF9 cell, or a yeast cell, e.g. *Saccharomyces cerevisiae* or *Pichia pastoris*, or any of the host cells mentioned hereinafter.

Covalent in vitro coupling of sugar moieties (such as dextran) to amino acid residues of the variant polypeptide may also be used, e.g. as described, for example in WO 87/05330 and in Aplin et al., *CRC Crit Rev. Biochem, pp.* 259-306, 1981. See also WO 03/093465 for further information on in vitro glycosylation of variants of FVII or FVIIa.

Attachment of Serine Protease Inhibitor

Attachment of a serine protease inhibitor can be performed in accordance with the method described in WO 96/12800.

Methods of Preparing a Polypeptide Variant of the Invention

The polypeptide variant of the present invention, optionally in glycosylated form, may be produced by any suitable method known in the art. Such methods include constructing a nucleotide sequence encoding the polypeptide variant and expressing the sequence in a suitable transformed or transfected host. Preferably, the host cell is a gamma-carboxylating host cell such as a mammalian cell. However, polypeptide variants of the invention may be produced, albeit less efficiently, by chemical synthesis or a combination of chemical synthesis or a combination of chemical synthesis and recombinant DNA technology.

A nucleotide sequence encoding a polypeptide of the invention may be constructed by isolating or synthesizing a nucleotide sequence encoding the parent FVII, such as hFVII with the amino acid sequence shown in SEQ ID NO:1 and then changing the nucleotide sequence so as to effect introduction (i.e. insertion or substitution) or removal (i.e. deletion or substitution) of the relevant amino acid residue(s).

The nucleotide sequence is conveniently modified by site-directed mutagenesis in accordance with conventional methods. Alternatively, the nucleotide sequence is prepared by chemical synthesis, e.g. by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR (polymerase chain reaction), ligation or ligation chain reaction (LCR) (Barany, *Proc Natl Acad Sci USA* 88:189-193, 1991). The individual oligonucleotides typically contain 5' or 3' overhangs for complementary assembly.

Once assembled (by synthesis, site-directed mutagenesis or another method), the nucleotide sequence encoding the polypeptide is inserted into a recombinant vector and operably linked to control sequences necessary for expression of the FVII in the desired transformed host cell.

Persons skilled in the art will be capable of selecting suitable vectors, expression control sequences and hosts for expressing the polypeptide. The recombinant vector may be an autonomously replicating vector, i.e. a vector, which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector, in which the nucleotide sequence encoding the polypeptide variant of the invention is operably linked to additional segments required for transcription of the nucleotide sequence. The vector is typically derived from plasmid or viral DNA. A number of suitable expression vectors for expression in the host cells mentioned herein are commercially available or described in the literature. Detailed information on suitable vectors for expressing FVII may be found in WO 01/58935, incorporated by reference.

The term "control sequences" is defined herein to include all components which are necessary or advantageous for the expression of the polypeptide variant of the invention. Each control sequence may be native or foreign to the nucleic acid sequence encoding the polypeptide variant. Such control sequences include, but are not limited to, a leader sequence, polyadenylation sequence, propeptide sequence, promoter, enhancer or upstream activating sequence, signal peptide sequence, and transcription terminator. At a minimum, the control sequences include a promoter.

A wide variety of expression control sequences may be used in the present invention, e.g. any of the control sequences disclosed in WO 01/58935, incorporated by reference.

The nucleotide sequence of the invention encoding a polypeptide variant, whether prepared by site-directed mutagenesis, synthesis, PCR or other methods, may optionally include a nucleotide sequence that encode a signal peptide. The signal peptide is present when the polypeptide variant is to be secreted from the cells in which it is expressed. Such signal peptide, if present, should be one recognized by the cell chosen for expression of the polypeptide variant. The signal peptide may be homologous (i.e. normally associated with hFVII) or heterologous (i.e. originating from another source than hFVII) to the polypeptide or may be homologous or heterologous to the host cell, i.e. a signal peptide normally expressed from the host cell or one which is not normally expressed from the host cell. For further information on suitable signal peptides, see WO 01/58935.

Any suitable host may be used to produce the polypeptide variant, including bacteria (although not particularly preferred), fungi (including yeasts), plant, insect, mammal, or other appropriate animal cells or cell lines, as well as transgenic animals or plants. Mammalian cells are preferred. Examples of bacterial host cells include gram-positive bacteria such as strains of *Bacillus*, e.g. *B. brevis* or *B. subtilis*, *Pseudomonas* or *Streptomyces*, or gram-negative bacteria, such as strains of *E. coli*. Examples of suitable filamentous fungal host cells include strains of *Aspergillus*, e.g. *A. oryzae*, *A. niger*, or *A. nidulans*, *Fusarium* or *Trichoderma*. Examples of suitable yeast host cells include strains of *Saccharomyces*, e.g. *S. cerevisiae*, *Schizosaccharomyces*, *Klyveromyces*, *Pichia*, such as *P. pastoris* or *P. methanolica*, *Hansenula*, such as *H. Polymorpha* or *Yarrowia*. Examples of suitable insect host cells include a *Lepidoptora* cell line, such as *Spodoptera frugiperda* (Sf9 or Sf21) or *Trichoplusioa ni* cells (High Five) (U.S. Pat. No. 5,077,214). Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)). Additional suitable cell lines are known in the art and available from public depositories such as the American Type Culture Collection, Rockville, Md. Also, mammalian cells, such as a CHO cell, may be modified to express sialyltransferase, e.g. 1,6-sialyltransferase, e.g. as described in U.S. Pat. No. 5,047,335, in order to provide improved glycosylation of the polypeptide variant.

In order to increase secretion it may be of particular interest to produce the polypeptide variant of the invention together with an endoprotease, in particular a PACE (paired basic amino acid converting enzyme) (e.g. as described in U.S. Pat. No. 5,986,079), such as a Kex2 endoprotease (e.g. as described in WO 00/28065).

Methods for introducing exogenous DNA into the above cell types, as well as other information regarding expression, production and purification of FVII variants, is found in WO 01/58935, incorporated herein by reference.

Pharmaceutical Composition of the Invention and its Use

In a further aspect, the present invention relates to a composition, in particular to a pharmaceutical composition, comprising a polypeptide variant of the invention and a pharmaceutically acceptable carrier or excipient.

The polypeptide variant or the pharmaceutical composition according to the invention may be used as a medicament.

Due to the improved properties mentioned above, the polypeptide variants of the invention, or the pharmaceutical composition of the invention, are particular useful for the treatment of uncontrollable bleeding events in trauma patients, thrombocytopenic patients, patients in anticoagulant treatment, and cirrhosis patients with variceal bleeding, or other upper gastrointestinal bleedings, in patients undergoing orthotopic liver transplantation or liver resection (allowing for transfusion free surgery), or in hemophilia patients.

Trauma is defined as an injury to living tissue caused by an extrinsic agent. It is the $4^{th}$ leading cause of death in the US and places a large financial burden on the economy.

Trauma is classified as either blunt or penetrative. Blunt trauma results in internal compression, organ damage and internal haemorrhage whereas penetrative trauma (as the consequence of an agent penetrating the body and destroying tissue, vessels and organs) results in external haemorrhage.

Trauma may be caused by numerous events, e.g. traffic accidents, gunshot wounds, falls, machinery accidents, and stab wounds.

Cirrhosis of the liver may be caused by direct liver injury, including chronic alcoholism, chronic viral hepatitis (types B, C, and D), and autoimmune hepatitis as well as by indirect injury by way of bile duct damage, including primary biliary cirrhosis, primary sclerosing cholangitis and biliary atresia. Less common causes of cirrhosis include direct liver injury from inherited disease such as cystic fibrosis, alpha-1-antitrypsin deficiency, hemochromatosis, Wilson's disease, galactosemia, and glycogen storage disease. Transplantation is the key intervention for treating late stage cirrhotic patients Thus, in a further aspect the present invention relates to a polypeptide variant of the invention for the manufacture of a medicament for the treatment of diseases or disorder wherein clot formation is desirable. A still further aspect of the present invention relates to a method for treating a mammal having a disease or disorder wherein clot formation is desirable, comprising administering to a mammal in need thereof an effective amount of the polypeptide variant or the pharmaceutical composition of the invention.

Examples of diseases/disorders wherein increased clot formation is desirable include, but is not limited to, hemorrhages, including brain hemorrhages, as well as patient with severe uncontrolled bleedings, such as trauma. Further examples include patients undergoing living transplantations, patients undergoing resection and patients with variceal bleeding. Another widespread disease/disorder in which it is contemplated that the polypeptides of the invention will be useful for increased clot formation is hemophilia, e.g. von Willebrand disease, hemophilia A, hemophilia B or hemophilia C.

As mentioned above, one particular aspect of the invention relates to use of the polypeptide variants of the invention for the treatment of intracerebral haemorrhage (ICH) or traumatic brain injury (TBI).

Among US and European populations, an estimated 10-15% of all stroke cases are caused by intracerebral haemorrhage, also known as brain haemorrhage, intracranial haemorrhage or haemorrhagic stroke, while the figure for Asian populations is estimated to be 20-30%. ICH is the most deadly form of stroke, for which there currently is no proven effective treatment. In addition to high short-term mortality rates, ICH also results in very high rates of severe mental and physical disability among survivors.

ICH can be distinguished from other types of stroke using a CT scan or MRI, after which treatment may be initiated, although until now the available treatment options have only been symptomatic and largely ineffective. If initiated sufficiently early, however, e.g. within about 3-4 hours of the onset of the haemorrhagic stroke, it is contemplated that treatment with the polypeptide variants of the invention may result in significant improvements in terms of increase survival rates and/or decreased disability rates. In particular, it is contemplated that an increased TF-independent activity, optionally with a reduced TF-dependent activity, obtained by use of the polypeptide variants of the invention, may be advantageous over rhFVIIa (NovoSeven®) by reducing or eliminating the risk of thromboembolic events.

Traumatic brain injury is another public health problem with high mortality rates and a high frequency of long-term disability. In the United States alone, there are an estimated 500,000 cases of TBI each year, and also here there is a lack of proven, effective treatments. The available data on clinical trials in head injury is reviewed by Narayan et al., *J. Neurotrama* (2002) 19(5):503-557.

One embodiment of this aspect of the invention thus relates to a method for treating ICH or TBI, comprising administering to a patient in need thereof an effective amount of a polypeptide variant of the invention as otherwise described above. Another embodiment of this aspect of the invention relates to use of a polypeptide of the invention for the manufacture of a medicament for the treatment of ICH or TBI.

In one embodiment, this aspect of the invention may generally be defined as a method for treating intracerebral haemorrhage or traumatic brain injury, comprising administering to a patient in need thereof an effective amount of a Factor VII (FVII) or Factor VIIa (FVIIa) polypeptide variant having an amino acid sequence comprising 1-15 amino acid modifications relative to human Factor VII (hFVII) or human Factor VIIa (hFVIIa) with the amino acid sequence shown in SEQ ID NO:1, wherein the FX activation activity of the polypeptide variant, in its activated form, is greater than the FX activation activity of rhFVIIa when assayed in the "TF-independent Factor X Activation Assay" disclosed herein. In particular, the ratio between the FX activation activity of the polypeptide variant, in its activated form, and the FX activation activity of rhFVIIa is preferably at least about 5, more preferably at least about 10, such as at least about 15.

Further, in addition to use of the variants described above, i.e. comprising at least one modification selected from (a) introduction of a hydrophobic amino acid residue by substitution in position 34, and (b) an amino acid substitution in position 36, for the treatment of ICH or TBI, it is also contemplated that certain other FVIIa variants having increased efficacy and preferably a decreased TF-dependent activity may be advantageous over rhFVIIa for these indications. These variants have an amino acid sequence comprising 1-15 amino acid modifications relative to human Factor VII (hFVII) or human Factor VIIa (hFVIIa) with the amino acid sequence shown in SEQ ID NO:1, and comprise an amino acid substitution in position 10 and/or 32, and optionally at least one further substitution to introduce an in vivo N-glycosylation site. Preferably, the substitution in position 10 is P10Q and the substitution in position 32 is K32E. More preferably, the variant includes both substitutions P10Q and K32E, and optionally one or more additional substitutions to introduce at least one in vivo N-glycosylation site, e.g. one, two or three glycosylation sites, preferably two glycosylation sites, selected from A51N, G58N, T106N, K109N, G124N, K143N+N145T, A175T, I205S, I205T, V253N, T267N, T267N+S269T, S314N+K316S, S314N+K316T, R315N+V317S, R315N+V317T, K316N+G318S, K316N+G318T, G318N and D334N. Still more preferably, the variant includes the substitutions P10Q and K32E as well as two substitutions selected from T106N, I205S/T and V253N, most preferably P10Q+K32E+T106N+V253N. The polypeptide variants of the invention are administered to patients in a therapeutically effective dose, normally one approximately paralleling that employed in therapy with rFVII such as NovoSeven®. By "therapeutically effective dose" herein is meant a dose that is sufficient to produce the desired effects in relation to the condition for which it is administered. The exact dose will depend on the circumstances, and will be ascertainable by one skilled in the art using known techniques. Normally, the dose should be capable of preventing or lessening the severity or spread of the condition or indication being treated. It will be apparent to those of skill in the art that an effective amount of a polypeptide variant or composition of the invention depends, inter alia, upon the disease, the dose, the administration schedule, whether the polypeptide variant or composition is administered alone or in conjunction with other therapeutic agents, the plasma half-life of the compositions, and the general health of the patient.

It is contemplated that a suitable dose of the variants of the invention for treatment of ICH, or TBI or other trauma, will be in the range of about 20-300 µg protein per kg body weight, e.g. about 30-250 µg/kg, such as about 40-200 µg/kg, e.g. about 60-150 µg/kg. For ICH, only a single dose of the of the variants of the invention will generally be indicated, while for TBI or other forms of trauma one or more additional doses may in certain cases be given as needed. Similar dose ranges are also applicable to hemophilia.

The polypeptide variant of the invention is preferably administered in a composition including a pharmaceutically acceptable carrier or excipient. "Pharmaceutically acceptable" means a carrier or excipient that does not cause any untoward effects in patients to whom it is administered. Such pharmaceutically acceptable carriers and excipients as well as suitable pharmaceutical formulation methods are well known in the art (see, for example, Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

The polypeptide variant of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

The pharmaceutical composition of the invention may be administered alone or in conjunction with other therapeutic agents. These agents may be incorporated as part of the same pharmaceutical composition or may be administered separately from the polypeptide variant of the invention, either concurrently or in accordance with another treatment schedule. In addition, the polypeptide variant or pharmaceutical composition of the invention may be used as an adjuvant to other therapies.

A "patient" for the purposes of the present invention includes both humans and other mammals. Thus, the methods are applicable to both human therapy and veterinary applications, in particular to human therapy.

The pharmaceutical composition comprising the polypeptide variant of the invention may be formulated in a variety of forms, e.g. as a liquid, gel, lyophilized, or as a compressed solid. The preferred form will depend upon the particular indication being treated and will be apparent to one skilled in the art.

In particular, the pharmaceutical composition comprising the polypeptide variant of the invention may be formulated in lyophilised or stable soluble form. The polypeptide variant may be lyophilised by a variety of procedures known in the art. The polypeptide variant may be in a stable soluble form by the removal or shielding of proteolytic degradation sites as described herein. The advantage of obtaining a stable soluble preparation lies in easier handling for the patient and, in the case of emergencies, quicker action, which potentially can become life saving. The preferred form will depend upon the particular indication being treated and will be apparent to one of skill in the art.

The administration of the formulations of the present invention can be performed in a variety of ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner. The formulations can be administered continuously by infusion, although bolus injection is acceptable, using techniques well known in the art, such as pumps or implantation. In some instances the formulations may be directly applied as a solution or spray.

Parentals

A preferred example of a pharmaceutical composition is a solution, in particular an aqueous solution, designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide variant having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic surfactants or detergents, antioxidants, and/or other miscellaneous additives such as bulking agents or fillers, chelating agents, antioxidants and cosolvents.

Detailed information on parental formulations suitable for administration of FVII variants, as well as sustained release preparations, is found in WO 01/58935 and WO 03/093465, incorporated herein by reference.

The invention is further described by the following non-limiting examples.

Materials and Methods

Active Site Region

The active site region is defined as any residues having at least one atom within 10 Å of any atom in the catalytic triad (residues H193, D242, S344).

Measurement of Reduced Sensitivity to Proteolytic Degradation

Proteolytic degradation can be measured using the assay described in U.S. Pat. No. 5,580,560, Example 5, where proteolysis is autoproteolysis.

Furthermore, reduced proteolysis can be tested in an in vivo model using radiolabelled samples and comparing proteolysis of rhFVIIa and the polypeptide variant of the invention by withdrawing blood samples and subjecting these to SDS-PAGE and autoradiography.

Irrespective of the assay used for determining proteolytic degradation, "reduced proteolytic degradation" is intended to mean a measurable reduction in cleavage compared to that obtained by rhFVIIa as measured by gel scanning of Coomassie stained SDS-PAGE gels, HPLC or as measured by conserved catalytic activity in comparison to wild type using the tissue factor independent activity assay described below.

Determination of the Molecular Weight of Polypeptide Variants

The molecular weight of polypeptide variants is determined by either SDS-PAGE, gel filtration, Western Blots, matrix assisted laser desorption mass spectrometry or equilibrium centrifugation, e.g. SDS-PAGE according to Laemmli, U.K., *Nature* Vol 227 (1970), pp. 680-85.

Determination of Phospholipid Membrane Binding Affinity

Phospholipid membrane binding affinity may be determined as described in Nelsestuen et al., *Biochemistry*, 1977; 30; 10819-10824 or as described in Example 1 in U.S. Pat. No. 6,017,882.

TF-Independent Factor X Activation Assay

This assay has been described in detail on page 39826 in Nelsestuen et al., *J Biol Chem*, 2001; 276:39825-39831.

Briefly, the molecule to be assayed (either hFVIIa, rhFVIIa or the polypeptide variant of the invention in its activated form) is mixed with a source of phospholipid (preferably phosphatidylcholine and phosphatidylserine in a ratio of 8:2) and relipidated Factor X in Tris buffer containing BSA. After a specified incubation time the reaction is stopped by addition of excess EDTA. The concentration of factor Xa is then measured from absorbance change at 405 nm after addition of a chromogenic substrate (S-2222, Chromogenix). After correction for background the tissue factor independent activity of rhFVIIa ($a_{wt}$) is determined as the absorbance change after 10 minutes and the tissue factor independent activity of the polypeptide variant of the invention ($a_{variant}$) is also determined as the absorbance change after 10 minutes. The ratio between the activity of the polypeptide variant, in its activated form, and the activity of rhFVIIa is defined as $a_{variant}/a_{wt}$.

Clotting Assay

The clotting activity of the FVIIa and variants thereof were measured in one-stage assays and the clotting times were recorded on a Thrombotrack IV coagulometer (Medinor). Factor VII-depleted human plasma (American Diagnostica) was reconstituted and equilibrated at room temperature for 15-20 minutes. 50 microliters of plasma was then transferred to the coagulometer cups.

FVIIa and variants thereof were diluted in Glyoxaline Buffer (5.7 mM barbiturate, 4.3 mM sodium citrate, 117 mM NaCl, 1 mg/ml BSA, pH 7.35). The samples were added to the cup in 50 ul and incubated at 37° C. for 2 minutes.

Thromboplastin (Medinor) was reconstituted with water and $CaCl_2$ was added to a final concentration of 4.5 mM. The reaction was initiated by adding 100 µl thromboplastin.

To measure the clotting activity in the absence of TF the same assay was used without addition of thromboplastin. Data was analysed using PRISM software.

Whole Blood Assay

The clotting activity of FVIIa and variants thereof were measured in one-stage assays and the clotting times were recorded on a Thrombotrack IV coagulometer (Medinor). 100 µl of FVIIa or variants thereof were diluted in a buffer containing 10 mM glycylglycine, 50 mM NaCl, 37.5 mM $CaCl_2$, pH 7.35 and transferred to the reaction cup. The clotting reaction was initiated by addition of 50 µL blood containing 10% 0.13 M tri-sodium citrate as anticoagulant. Data was analysed using Excel or PRISM software.

Amidolytic Assay

The ability of the variants to cleave small peptide substrates can be measured using the chromogenic substrate S-2288 (D-Ile-Pro-Arg-p-nitroanilide). FVIIa is diluted to about 10-90 nM in assay buffer (50 mM Na-Hepes pH 7.5, 150 mM NaCl, 5 mM $CaCl_2$, 0.1% BSA, 1 U/ml Heparin). Furthermore, soluble TF (sTF) is diluted to 50-450 nM in assay buffer. 120 µl of assay buffer is mixed with 20 µl of the FVIIa sample and 20 µl sTF. After 5 min incubation at room temperature with gentle shaking, followed by 10 min incubation at 37° C., the reaction is started by addition of the S-2288 substrate to 1 mM and the absorption at 405 nm is determined at several time points.

ELISA Assay

FVII/FVIIa (or variant) concentrations are determined by ELISA. Wells of a microtiter plate are coated with an antibody directed against the protease domain using a solution of 2 µg/ml in PBS (100 µl per well). After overnight coating at R.T. (room temperature), the wells are washed 4 times with THT buffer (100 mM NaCl, 50 mM Tris-HCl pH 7.2 0.05% Tween® 20). Subsequently, 200 µl of 1% Casein (diluted from 2.5% stock using 100 mM NaCl, 50 mM Tris-HCl pH 7.2) is added per well for blocking. After 1 hr incubation at R.T., the wells are emptied, and 100 µl of sample (optionally diluted in dilution buffer (THT+0.1% Casein)) is added. After another incubation of 1 hr at room temperature, the wells are washed 4 times with THT buffer, and 100 µl of a biotin-labelled antibody directed against the EGF-like domain (1 µg/ml) is added. After another 1 hr incubation at R.T., followed by 4 more washes with THT buffer, 100 µl of streptavidin-horse radish peroxidase (DAKO A/S, Glostrup, Denmark, 1/10000 diluted) is added. After another 1 hr incubation at R.T., followed by 4 more washes with THT buffer, 100 µl of TMB (3,3',5,5'-tetramethylbenzidine, Kem-en-Tech A/S, Denmark) is added. After 30 min incubation at R.T. in the dark, 100 µl of 1 M $H_2SO_4$ is added and $OD_{450nm}$ is determined. A standard curve is prepared using rhFVIIa (NovoSeven®).

Alternatively, FVII/FVIIa or variants may be quantified through the Gla domain rather than through the protease domain. In this ELISA set-up, wells are coated overnight with an antibody directed against the EGF-like domain and for detection, a calcium-dependent biotin-labelled monoclonal anti-Gla domain antibody is used (2 µg/ml, 100 µl per well). In this set-up, 5 mM $CaCl_2$ is added to the THT and dilution buffers.

Thrombogram Assay

The effect of hFVIIa, rhFVIIa or FVIIa variants on thrombin generation in human plasma is tested in a modified version of the assay described on page 589 in Hemker et al. (2000) *Thromb Haemost* 83:589-91. Briefly, the molecule to be assayed (either hFVIIa, rhFVIIa or a variant) is mixed with FVII-depleted platelet poor plasma (PPP) containing either relipidated recombinant tissue factor (such as Innovin from Dade Behring) or phospholipid (phosphatidylcholine and phosphatidylserine in a ratio of 8:2, or phosphatidylcholine, phosphatidylserine and phosphatidylethanol in a ratio of 4:2:4).

The reaction is started by addition of a fluoregenic thrombin substrate and calcium chloride. The fluorescence is measured continuously and the thrombin amidolytic activity is determined by calculating the slope of the fluorescence curve (the increase in fluorescence over time). In this way the time until maximum thrombin amidolytic activity is obtained ($T_{max}$), and the thrombin generation rate (maximal increase in thrombin activity) and the total thrombin work (area under the curve (AUC)) can be calculated.

Frozen citrated FVII-depeleted plasma is thawed in the presence of corn trypsin inhibitor (100 µg/ml serum) to inhibit the contact pathway of coagulation. To each well of a 96-well microtiter plate is added 80 µl plasma and 20 µl buffer containing rhFVII or variant to be tested in final concentrations of between 0.1 and 100 nM. Recombinant human tissue factor (rTF) is added in 5 µl assay buffer to a final concentration of 1 pM. The assay buffer consists of 20 mM Hepes, 150 mM NaCl and 60 mg/ml BSA in distilled water. The reaction is started by adding 20 µl of the substrate solution containing 0.1 M calcium chloride. The assay plate and reagents are pre-warmed to 37° C. and the reaction takes place at this temperature. The fluorimeter used is a BMG Fluormeter with an excitation filter at 390 nm and an emission filter at 460 nm. The fluorescence is measured in each well of 96-well clear bottom plates at 20-40 second intervals over 30-180 minutes. Data are analyzed using PRISM Software.

Tissue Factor Binding Surface Plasmon Resonance Assay (Biacore Assay)

Surface plasmon resonance analysis was used to determine the relative binding of wild-type Factor VIIa and variants thereof to soluble tissue factor. Recombinant soluble tissue factor that contains the extracellular domain was coupled to 270 response units on a Biacore CM5 chip using NHS/EDC coupling. Soluble tissue factor was coupled at a pH of 4.5 to enable interaction with the chip surface.

In this assay, tissue factor binding of factor VII protein was compared at a single concentration of FVIIa or variant to allow a relative comparison of the variants to wild-type. This concentration was determined by means of a standard curve of wild type FVIIa that was flowed over the chip in concentrations between 75 and 0 µg/ml. FVIIa was removed by addition of 10 mM EDTA. It was determined in this manner that a concentration of 15 µg/ml gave binding in the linear range. Variants of FVIIa were then flowed over the chip at 15 µg/ml to determine the relative binding strength of FVIIa or variants to tissue factor.

EXAMPLES

Example 1

The X-ray structure of hFVIIa in complex with soluble tissue factor by Banner et al., *J Mol Biol*, 1996; 285:2089 is used for this example. For further information on the calculations in this example, see WO 01/58935.

Surface Exposure

Performing fractional ASA calculations resulted in the following residues being determined to have more than 25% of their side chain exposed to the surface: A1, N2, A3, F4, L5, E6, E7, L8, R9, P10, S12, L13, E14, E16, K18, E19, E20, Q21, S23, F24, E25, E26, R28, E29, F31, K32, D33, A34, E35, R36, K38, L39, W41, I42, S43, S45, G47, D48, Q49, A51, S52, S53, Q56, G58, S60, K62, D63, Q64, L65, Q66, S67, I69, F71, L73, P74, A75, E77, G78, R79, E82, T83, H84, K85, D86, D87, Q88, L89, I90, V92, N93, E94, G97, E99, S103, D104, H105, T106, G107, T108, K109, S111, R113, E116, G117, S119, L120, L121, A122, D123, G124, V125, S126, T128, P129, T130, V131, E132, I140, L141, E142, K143, R144, N145, A146, S147, K148, P149, Q150, G151, R152, G155, K157, V158, P160, K161, E163, L171, N173, G174, A175, N184, T185, I186, H193, K197, K199, N200, R202, N203, I205, S214, E215, H216, D217, G218, D219, S222, R224, S232, T233, V235, P236, G237, T238, T239, N240, H249, Q250, P251, V253, T255, D256, E265, R266, T267, E270, R271, F275, V276, R277, F278, L280, L287, L288, D289, R290, G291, A292, T293, L295, E296, N301, M306, T307, Q308, D309, L311, Q312, Q313, R315, K316, V317, G318, D319, S320, P321, N322, T324, E325, Y326, Y332, S333, D334, S336, K337, K341, G342, H351, R353, G354, Q366, G367, T370, V371, G372, R379, E385, Q388, K389, R392, S393, E394, P395, R396, P397, G398, V399, L400, L401, R402, P404 and P406 (A1-S45 are located in the Gla domain, the remaining positions are located outside the Gla domain).

The following residues were determined to have more than 50% of their side chain exposed to the surface: A1, A3, F4, L5, E6, E7, L8, R9, P10, E14, E16, K18, E19, E20, Q21, S23, E25, E26, E29, K32, A34, E35, R36, K38, L39, I42, S43, G47, D48, A51, S52, S53, Q56, G58, S60, K62, L65, Q66, S67, I69, F71, L73, P74, A75, E77, G78, R79, E82, H84, K85, D86, D87, Q88, L89, I90, V92, N93, E94, G97, T106, G107, T108, K109, S111, E116, S119, L121, A122, D123, G124, V131, E132, L141, E142, K143, R144, N145, A146, S147, K148, P149, Q150, G151, R152, G155, K157, P160, N173, G174, A175, K197, K199, N200, R202, S214, E215, H216, G218, R224, V235, P236, G237, T238, H249, Q250, V253, D256, T267, F275, R277, F278, L288, D289, R290, G291, A292, T293, L295, N301, M306, Q308, D309, L311, Q312, Q313, R315, K316, G318, D319, N322, E325, D334, K341, G354, G367, V371, E385, K389, R392, E394, R396, P397, G398, R402, P404 and P406 (A1-S43 are located in the Gla domain, the remaining positions are located outside the Gla domain).

Tissue Factor Binding Site

It was determined using ASA calculations that the following residues in hFVII change their ASA in the complex. These residues were defined as constituting the receptor binding site: L13, K18, F31, E35, R36, L39, F40, I42, S43, S60, K62, D63, Q64, L65, I69, C70, F71, C72, L73, P74, F76, E77, G78, R79, E82, K85, Q88, I90, V92, N93, E94, R271, A274, F275, V276, R277, F278, R304, L305, M306, T307, Q308, D309, Q312, Q313, E325 and R379.

Active Site Region

The active site region is defined as any residue having at least one atom within a distance of 10 Å from any atom in the catalytic triad (residues H193, D242, S344): I153, Q167, V168, L169, L170, L171, Q176, L177, C178, G179, G180, T181, V188, V189, S190. A191, A192, H193, C194, F195, D196, K197, I198, W201, V228, I229, I230, P231, S232, T233, Y234, V235, P236, G237, T238, T239, N240, H241, D242, I243, A244, L245, L246, V281, S282, G283, W284, G285, Q286, T293, T324, E325, Y326, M327, F328, D338, S339, C340, K341, G342, D343, S344, G345, G346, P347, H348, L358, T359, G360, I361, V362, S363, W364, G365, C368, V376, Y377, T378, R379, V380, Q382, Y383, W386, L387, L400, and F405.

The Ridge of the Active Site Binding Cleft

The ridge of the active site binding cleft region was defined by visual inspection of the FVIIa structure 1FAK.pdb as: N173, A175, K199, N200, N203, D289, R290, G291, A292, P321 and T370.

Example 2

Design of an Expression Cassette for Expression of rhFVII in Mammalian Cells

The expression cassette for expression of rhFVII was designed and cloned as described in Example 2 of WO 01/58935.

Example 3

Construction of Expression Cassette Encoding Variants of the Invention

Sequence overhang extension (SOE) PCR was used for generating constructs having variant FVII open reading frames with substituted codons by using standard methods.

Example 4

Expression of Polypeptide Variants in CHO K1 Cells

The cell line CHO K1 (ATCC # CCL-61) is seeded at 50% confluence in T-25 flasks using MEMα, 10% FCS (Gibco/BRL Cat #10091), P/S and 5 µg/ml phylloquinone and allowed to grow until confluent. The confluent mono cell layer is transfected with 5 µg of the relevant plasmid described above using the Lipofectamine 2000 transfection agent (Life Technologies) according to the manufacturer's instructions. Twenty four hours post transfection a sample is drawn and quantified using e.g. an ELISA recognizing the EGF1 domain of hFVII. At this time point relevant selection (e.g. Hygromycin B) may be applied to the cells with the purpose of generating a pool of stable transfectants. When using CHO K1 cells and the Hygromycin B resistance gene as selectable marker on the plasmid, this is usually achieved within one week.

Example 5

Generation of CHO K1 Cells Stably Expressing Polypeptide Variants

A vial of CHO-K1 transfectant pool is thawed and the cells seeded in a 175 cm² tissue flask containing 25 ml of MEMα, 10% FCS, phylloquinone (5 µg/ml), 100 U/l penicillin, 100 µg/l streptomycin and grown for 24 hours. The cells are harvested, diluted and plated in 96-well microtiter plates at a cell density of ½-1 cell/well. After a week of growth, colonies of 20-100 cells are present in the wells and those wells containing only one colony are labelled. After a further two weeks, the media in all wells containing only one colony is substituted with 200 µl fresh medium. After 24 hours, a medium sample is withdrawn and analysed by e.g. ELISA. High producing clones are selected and used for large scale production of FVII or variants.

Example 6

Purification of Polypeptide Variants and Subsequent Activation

FVII and FVII variants are purified as follows: The procedure is performed at 4° C. The harvested culture media from large-scale production is ultrafiltered and subsequently diafiltered against 10 mM Tris pH 8.6, using a Millipore TFF system with 30 kDa cut-off Pellicon membranes. After concentration of the medium, citrate is added to 5 mM and the pH is adjusted to 8.6. If necessary, the conductivity is lowered to below 10 mS/cm. Alternatively, the media may be diluted and pH- and citrate-adjusted without prior ultra- and diafiltration. Subsequently, the sample is applied to a Q SEPHAROSE™ FF column, equilibrated with 50 mM NaCl, 10 mM Tris pH 8.6. After washing the column with 100 mM NaCl, 10 mM Tris pH 8.6, and for some variants 150 mM NaCl, 10 mM Tris pH 8.6, FVII is eluted using 10 mM Tris, 25 mM NaCl, 35 mM CaCl₂, pH 8.6. In the elution step, the concentration of CaCl₂ or NaCl can be increased if necessary to improve the yield.

For the second chromatographic step, an affinity column is prepared by coupling of a monoclonal Calcium-dependent anti-Gla-domain antibody to CNBr-activated SEPHAROSE™ FF column. About 5.5 mg antibody is coupled per ml resin. The column is equilibrated with 10 mM Tris, up to 100 mM NaCl, 35 mM CaCl₂, pH 7.5. NaCl is for some variants added to the sample to a concentration of 100 mM NaCl and the pH is adjusted to 7.4-7.6. After O/N application of the sample, the column is washed with up to 100 mM NaCl, 35 mM CaCl₂, 10 mM Tris pH 7.5, and the FVII protein is eluted with 100 mM NaCl, 50 mM citrate, 75 mM Tris pH 7.5, or alternatively 10 mM Tris, 25 mM NaCl, 5 mM EDTA pH 8.6. The latter elution buffer allows for a direct load onto the third chromatographic column without any adjustment of the eluate.

For the third chromatographic step, the conductivity of the sample is lowered to below 10 mS/cm, if necessary, and the pH is adjusted to 8.6. The sample is then applied to an anion exchange column, typically a Q SEPHAROSE™ column at a density around 3-10 mg protein per ml gel or a Poros 50 HQ column (Applied BioSciences) at a density of 5-40 mg protein per ml gel to obtain efficient activation, both columns previously equilibrated with 25-50 mM NaCl, 10 mM Tris pH 8.6. After application, the column is washed with up to 50 mM NaCl, 0.25 mM CaCl₂, 10 mM Tris pH 8.6 for 2-4 hours with a flow of 3-4 column volumes (cv) per hour. The FVII protein is eluted using a gradient of 0-100% of 500 mM NaCl, 10 mM Tris pH 8.6 over 40 cv. FVII containing fractions are pooled.

For the final purification step either an anion exchange or a gel filtration step is used. For the anion exchange chromatographic step, the conductivity is lowered to below 10 mS/cm. Subsequently, the sample is applied to a Q SEPHAROSE™ column (equilibrated with 140 mM NaCl, 10 mM glycylglycine pH 8.6) at a concentration of 3-5 mg protein per ml gel. The column is then washed with 140 mM NaCl, 10 mM glycylglycine pH 8.6 and FVII is eluted with 140 mM NaCl, 15-35 mM CaCl₂, 10 mM glycylglycine pH 8.6. The eluate is diluted to 10 mM CaCl₂ and the pH is adjusted 6.8-7.2. Finally, Tween® 80 is added to 0.01% and the pH is adjusted to 5.5 for storage at −80° C. For the gel filtration step, a G25 column (HiPrep, Amersham Biosciences) is equilibrated and run in 10 mM glycylglycine, 10 mM CaCl₂, 140 mM NaCl, 0.01% Tween® 80, pH 5.5.

Example 7

Experimental Results—FX Activation Activity

Subjecting the variants of the invention to the "TF-independent Factor X Activation Assay", the following results were obtained (the results being expressed as a percentage of the activity of the P10Q+K32E variant as a reference):

TABLE 1

| Variant | TF-independent FX activation $(a_{variant}/a_{P10QK32E}) * 100$ |
|---|---|
| rhFVIIa | 10 |
| P10Q + K32E (reference) | 100 |
| A3AY + P10Q + K32E + A34L | 216 |
| P10Q + K32E + D33F + A34E | 194 |
| P10Q + K32E + A34E + P74S | 190 |
| P10Q + K32E + A34E + R36E + K38E | 144 |
| P10Q + K32E + A34D + R36E | 140 |
| P10Q + K32E + A34E + R36E + T106N + V253N | 51 |

As it appears from the above results, the variants of the invention showed a substantial improvement in FX activation activity as compared to rhFVIIa and also as compared to [P10Q+K32E]rhFVIIa.

Example 8

Experimental Results—Clotting Activity in the "Whole Blood Assay"

Subjecting variants of the invention to the "Whole Blood Assay" revealed that they exhibited a significantly increased clotting activity (i.e. reduced clotting time) as compared to rhFVIIa as well as [P10Q+K32E]rhFVIIa. The experimental results are shown in FIG. 1 and Table 2 below.

TABLE 2

| Variant | Clotting time (Whole Blood Assay) $t_{variant}/t_{wt}$ |
|---|---|
| rhFVIIa (reference) | 1 |
| A3AY + P10Q + K32E + E116D | 0.4 |

TABLE 2-continued

| Variant | Clotting time (Whole Blood Assay) $t_{variant}/t_{wt}$ |
|---|---|
| A3AY + P10Q + K32E + A34L | 0.3 |
| P10Q + K32E + A34E + P74S | 0.3 |
| A3AY + P10Q + K32E + E77A | 0.4 |
| P10Q + K32E + A34E + R36E + T106N + V253N | 0.2 |

Example 9

Experimental Results—Clotting Activity in the "Clotting Assay"

When assayed in a TF-dependent clotting assay (the "Clotting Assay" described above in the Materials and Methods section) it was evident that variants of the invention having the R36E substitution have a significantly reduced clotting activity when compared to rhFVII or to other variants of the invention. See Table 3 below. Nevertheless, as illustrated in Example 7 above, variants having the R36E substitution have an increased Factor X activation activity in the "TF-independent Factor X Activation Assay".

TABLE 3

| Variant | Average Clotting Activity (units/mg$_{variant}$/units/mg$_{wt}$) (n = 2–3) |
|---|---|
| NovoSeven ® (reference) | 52,119 (100%) |
| P10Q + K32E | 52,714 (101%) |
| A3AY + P10Q + K32E + A34L | 56,948 (107%) |
| P10Q + K32E + A34E + R36E | 1,439 (2.7%) |
| P10Q + K32E + A34D + R36E + K38E | 1,232 (2.4%) |
| P10Q + K32E + A34E + R36E + T106N + V253N | 180 (<1%) |

Example 10

Experimental Results—Throbim Generation in the Thrombogram Assay

Using both phospholipid(PL)-dependent and tissue factor (TF)-dependent thrombograms (see the description of the Thrombogram Assay above), the maximum rate of thrombin generation was determined for FVIIa variants at different concentrations of variant proteins. By plotting the maximum thrombin generation rates (expressed as FU (fluorescence units) per sec$^2$) as a function of the variant concentration in pM, the results shown in FIG. 2 (maximum tissue factor-dependent thrombin generation rate) and FIG. 3 (maximum phospholipid-dependent thrombin generation rate) were obtained.

From these results it is evident that the FVIIa variant P10Q K32E A34E R36E has a differentiated thrombin generation ability depending on the whether the reaction is PL-dependent or TF-dependent. The maximum TF-dependent thrombin generation rate of this variant is decreased by approximately 10-fold (punctuated line in FIG. 2) when compared to the FVIIa variants P10Q K32E or A3AY P10Q K32E A34L. Also, lag time, time to peak, peak height and (to a lesser extent) AUC are reduced for P10Q K32E A34E R36E compared to the other variants (results not shown). In contrast to the TF-dependent activity, the PL-dependent activity of the P10Q K32E A34E R36E variant is equivalent to that of the other variants tested in this example (see FIG. 3), i.e. this variant has full PL-dependent activity even though the TF-dependent activity is substantially reduced.

Figure 2:
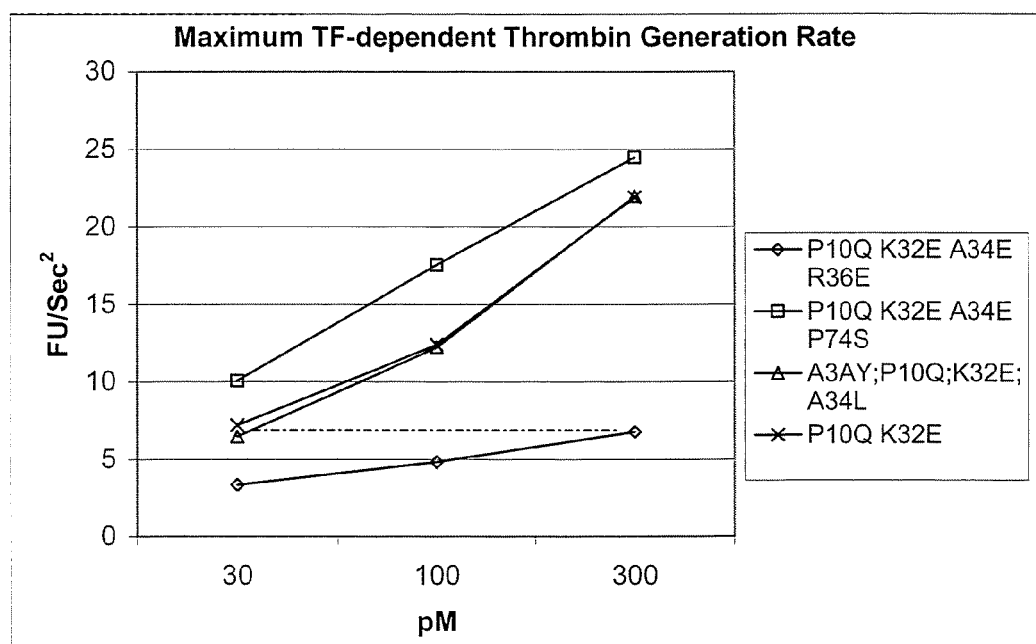
FIG. 2 shows the maximum tissue factor-dependent thrombin generation rate for variants of the invention determined in the "Thrombogram Assay".
Figure 3:
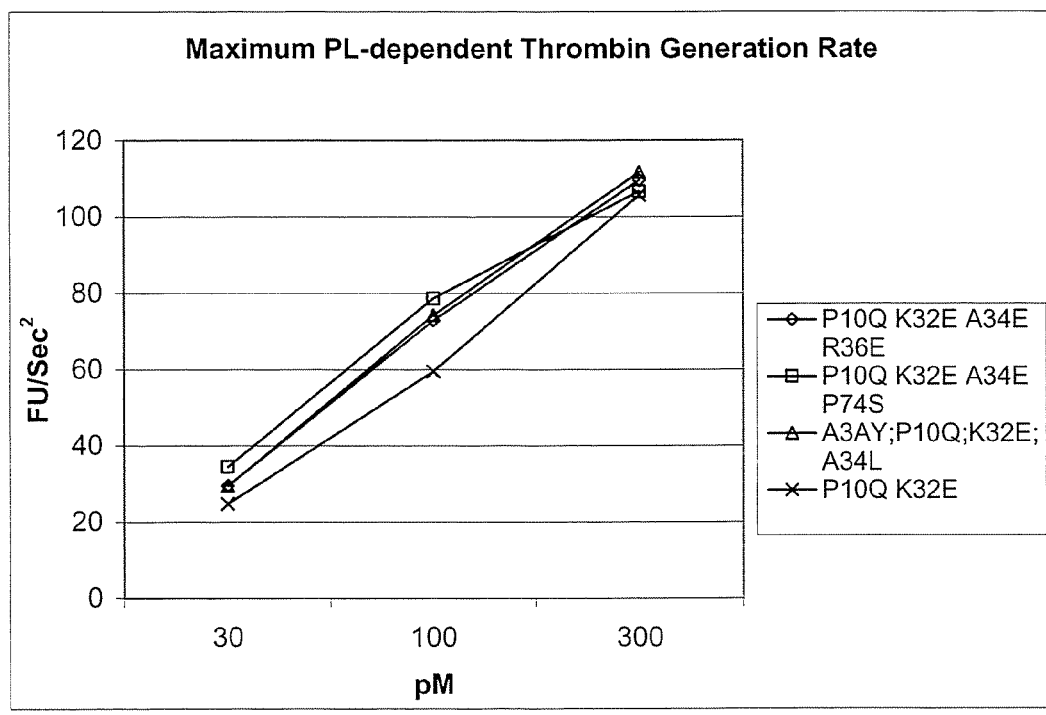
FIG. 3 shows the maximum phospholipid-dependent thrombin generation rate for variants of the invention determined in the "Thrombogram Assay".

In the same experiment, the variant P10Q K32E A34E R36E was compared directly to the variant P10Q K32E A34E P74S, which has a high TF-dependent thrombin generation rate as shown in FIG. 2. The differences in TF-binding between these two variants (i.e. the reduced TF-binding of the variant P10Q K32E A34E R36E) is believed to be directly attributable to the presence of the R36E substitution, possibly in synergy with the A34E substitution.

In addition, the PL-dependent and TF-dependent activity of the variant P10Q+K32E+A34E+R36E+T106N+V253N was compared to that of wild-type rhFVIIa (NovoSeven®). The results, in the form of thrombograms illustrating thrombin generation as a function of time, are shown in FIGS. 4 (PL-dependent activity) and 5 (TF-dependent activity).

Figure 4:
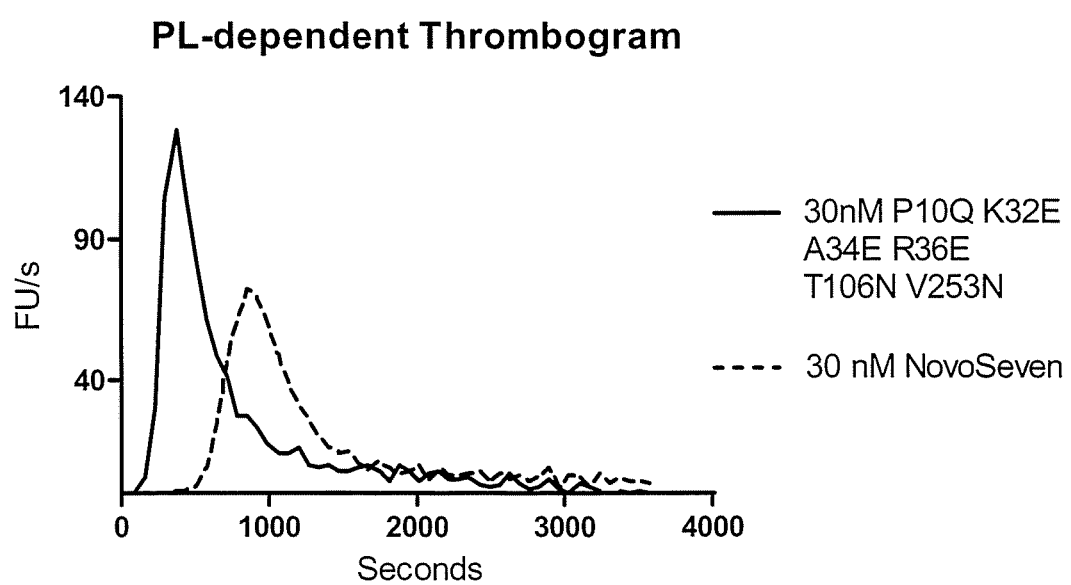
FIG. 4 is a thrombogram showing the phospholipid-dependent clotting activity of a variant of the invention (P10Q+K32E+A34E+R36E+T106N+V253N) compared to rhFVIIa (NovoSeven®).

FIG. 4 shows that the PL-dependent activity of the variant of the invention, compared to rhFVIIa, has a reduced lag time, a reduced time to peak, an increased peak height, and an increased maximum rate of thrombin generation. In contrast to the results for the PF-dependent activity, FIG. 5 shows that the TF-dependent activity of the variant of the invention, compared to rhFVIIa, has an increased lag time, an increased time to peak, a reduced peak height, and a reduced maximum rate of thrombin generation.

Figure 5:
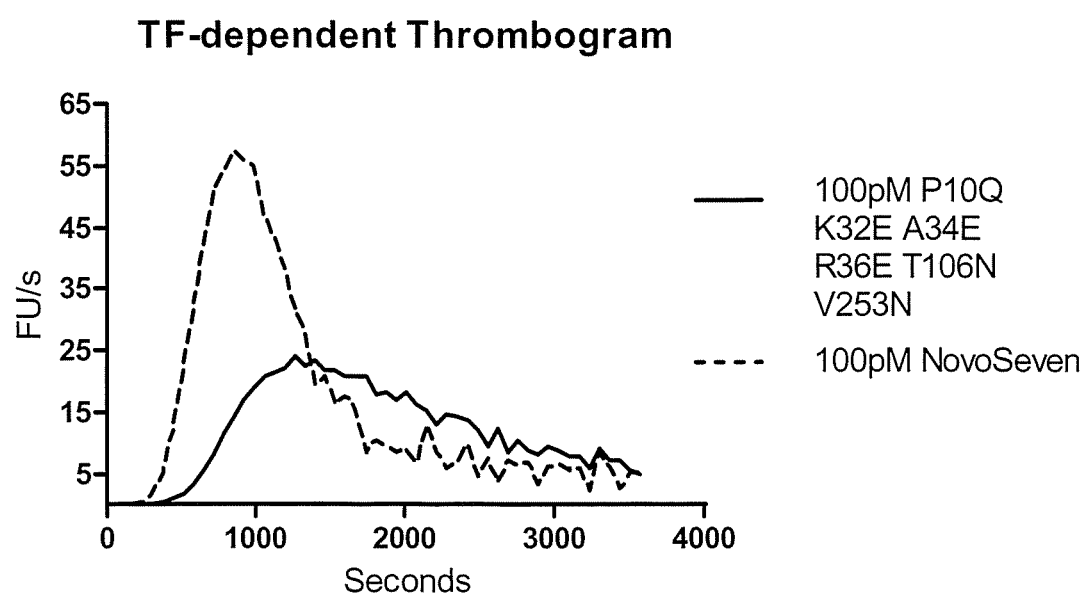
FIG. 5 is a thrombogram showing the tissue factor-dependent clotting activity of a variant of the invention (P10Q+K32E+A34E+R36E+T106N+V253N) compared to rhFVIIa (NovoSeven®).

Taken together, the results illustrated in FIGS. 4 and 5 show that the variant of the invention, P10Q+K32E+A34E+R36E+T106N+V253N, has an enhanced phospholipid-dependent activity and at the same time a reduced tissue factor-dependent activity compared to rhFVIIa. Both of these properties are contemplated to be advantageous in a clinical setting, e.g. in the case of trauma or intracerebral haemorrhage, the enhanced PL-dependent activity for obtaining faster and more effective blood clotting, and the reduced TF-dependent activity for minimizing the risk of undesired blood clot formation.

Example 11

Experimental Results—FVIIa Binding to Tissue Factor in the Biacore Assay

Subjecting variants of the invention to assay by surface plasmon resonance on a Biacore system using a TF chip as described in the Materials and Methods section, the following results were obtained:

TABLE 4

| Variant | Average response units (n = 5) |
|---|---|
| Wild-type FVIIa | 888 |
| P10Q; K32E | 714 |
| A3AY; P10Q; K32E; A34L | 967* |
| P10Q; K32E; A34E; R36E | 414 |

*n = 2

In consistency with the TF-dependent thrombin generation rate data from the Thrombogram Assay (Example 10), the results in Table 4 indicate that the R36E substitution confers less binding to tissue factor.

In the same Biacore Assay, FVIIa variants having the same modifications as the variants listed in Table 4 together with two additional modifications introducing two glycosylation sites (T106N and either V253N or I205T) were also tested for binding to tissue factor. The results are shown in Table 5 below.

TABLE 5

| Variant | Average response units (n = 5) |
|---|---|
| T106N; V253N | 717 |
| T106N; I205T | 612 |
| P10Q; K32E; T106N; I205T | 502 |
| P10Q; K32E; T106N; V253N | 498 |
| A3AY; P10Q; K32E; A34L; T106N; V253N | 522 |
| P10Q; K32E; A34E; R36E; T106N; I205T | 216 |

These results are consistent with those of Table 4 and show that compared to the same variants (or the wild-type) in Table 4 without the additional glycosylation sites, the presence of two new glycosylation sites in the variants of Table 5 provides a (further) reduction in tissue factor binding. As was the case for the variants of Table 4, the presence of the R36E substitution in a glycosylation variant also results in a level of tissue factor binding that is substantially lower than the tissue factor binding of the other glycosylation variants that do not have this substitution.

While the foregoing invention has been described in some detail for purposes of clarity and understanding, it will be clear to one skilled in the art from a reading of this disclosure that various changes in form and detail can be made without departing from the true scope of the invention. It is understood that the examples and embodiments described herein are for illustrative purposes only and that various modifications or changes in light thereof will be suggested to persons skilled in the art and are to be included within the spirit and purview of this application and scope of the appended claims. For example, all the techniques and apparatus described above may be used in various combinations. All publications, patents, patent applications, and/or other documents cited in this application are incorporated herein by reference in their entirety for all purposes to the same extent as if each individual publication, patent, patent application, and/or other document were individually indicated to be incorporated herein by reference in its entirety for all purposes.

The invention claimed is:

1. A method for treating a mammal having a disease or a disorder wherein clot formation is desirable, comprising administering to a mammal in need thereof an effective amount of a recombinant Factor VII (FVII) or Factor VIIa (FVIIa) polypeptide variant having clotting activity, said recombinant FVII or FVIIa polypeptide variant having at least 95% sequence identity to SEQ ID NO: 1, wherein the arginine residue at position 36 is substituted with a negatively charged amino acid residue, and wherein said disease or disorder is selected from the group consisting of hemorrhages, variceal bleeding, and hemophilia.

2. The method of claim 1, wherein said disease or disorder is hemophilia.

3. A method for treating intracerebral haemorrhage or traumatic brain injury, comprising administering to a patient in need thereof an effective amount of a recombinant Factor VII (FVII) or Factor VIIa (FVIIa) polypeptide variant having clotting activity, said recombinant FVII or FVIIa polypeptide variant having at least 95% sequence identity to SEQ ID NO: 1, wherein the arginine residue at position 36 is substituted with a negatively charged amino acid residue, and wherein amino acid positions of the variant are numbered relative to the amino acid sequence of SEQ ID NO: 1.

4. The method of claim 1, wherein the amino acid substitution in position 36 is R36D or R36E.

5. The method of claim 4, wherein the amino acid substitution in position 36 is R36E.

6. The method of claim 1, wherein the recombinant FVII or FVIIa polypeptide variant comprises an amino acid substitution in position 34.

7. The method of claim 6, wherein a negatively charged amino acid residue is substituted for the alanine residue in position 34 of the variant.

8. The method of claim 7, wherein the amino acid substitution in position 34 is A34E.

9. The method of claim 7, wherein the amino acid substitution in position 36 is R36E or R36D.

10. The method of claim 8, wherein the recombinant FVII or FVIIa polypeptide variant comprises the amino acid substitutions A34E+R36E or A34E+R36D.

11. The method of claim 10, wherein the recombinant FVII or FVIIa polypeptide variant comprises the amino acid substitutions A34E+R36E.

12. The method of claim 4, wherein the recombinant FVII or FVIIa polypeptide variant comprises an amino acid substitution in position 10 or 32.

13. The method of claim 12, wherein the recombinant FVII or FVIIa polypeptide variant comprises amino acid substitutions in positions 10 and 32.

14. The method of claim 13, wherein the amino acid substitution in position 32 is K32E.

15. The method of claim 14, wherein the amino acid substitution in position 10 is P10Q.

16. The method of claim 15, wherein the recombinant FVII or FVIIa polypeptide variant comprises the amino acid substitutions P10Q+K32E+R36E.

17. The method of claim 16, wherein the recombinant FVII or FVIIa polypeptide variant comprises an amino acid substitution in position 34.

18. The method of claim 17, wherein a negatively charged amino acid residue is substituted for the alanine residue in position 34.

19. The method of claim 18, wherein said substitution in position 34 is A34E.

20. The method of claim 1, wherein the recombinant FVII or FVIIa polypeptide variant comprises at least one introduced N-glycosylation site in a position located outside the Gla domain.

21. The method of claim 20, wherein the at least one introduced N-glycosylation site comprises at least one amino acid substitution selected from the group consisting of T106N, I205T, and V253N.

22. The method of claim 4, wherein the recombinant FVII or FVIIa polypeptide variant comprises at least one introduced N-glycosylation site in a position located outside the Gla domain.

23. The method of claim 22, wherein the at least one introduced N-glycosylation site comprises at least one amino acid substitution selected from the group consisting of T106N, I205T, and V253N.

24. The method of claim 1, wherein the recombinant FVII or FVIIa polypeptide variant comprises at least two introduced N-glycosylation sites selected from the group consisting of T106N, I205T, and V253N.

25. The method of claim 24, wherein the recombinant FVII or FVIIa polypeptide variant comprises the substitutions P10Q+K32E+A34E+R36E+T106N+V253N.

26. The method of claim 24, wherein the recombinant FVII or FVIIa polypeptide variant comprises the substitutions P10Q+K32E+A34E+R36E+T106N+I205T.

27. The method of claim 24, wherein the recombinant FVII or FVIIa polypeptide variant comprises the substitutions P10Q+K32E+A34E+R36E+I205T+V253N.

28. The method of claim 1, wherein the recombinant FVII or FVIIa polypeptide variant is in its activated form.

29. The method of claim 1, wherein said disease or disorder is hemorrhage.

30. The method of claim 1, wherein the recombinant FVII or FVIIa polypeptide variant comprises an amino acid sequence which differs from the amino acid sequence of hFVII or hFVIIa shown in SEQ ID NO: 1 in no more than 10 amino acid residues.

31. The method of claim 3, wherein the amino acid substitution in position 36 is R36D or R36E.

* * * * *

SEQUENCE LISTING

```
<160> NUMBER OF SEQ ID NOS: 1

<210> SEQ ID NO 1
<211> LENGTH: 406
<212> TYPE: PRT
<213> ORGANISM: Homo sapiens

<400> SEQUENCE: 1

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220
```

```
Val Ala Gln Val Ile Ile Pro Ser Thr Tyr Val Pro Gly Thr Thr Asn
225             230                 235             240

His Asp Ile Ala Leu Leu Arg Leu His Gln Pro Val Val Leu Thr Asp
            245                 250                 255

His Val Val Pro Leu Cys Leu Pro Glu Arg Thr Phe Ser Glu Arg Thr
                260                 265             270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305             310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
            355                 360                 365

Ala Thr Val Gly His Phe Gly Val Tyr Thr Arg Val Ser Gln Tyr Ile
        370                 375                 380

Glu Trp Leu Gln Lys Leu Met Arg Ser Glu Pro Arg Pro Gly Val Leu
385             390                 395                 400

Leu Arg Ala Pro Phe Pro
                405
```